(12) United States Patent
Worrel

(10) Patent No.: US 12,427,039 B2
(45) Date of Patent: Sep. 30, 2025

(54) GRAFT COMPRESSION SYSTEM

(71) Applicant: Daniel A. Worrel, Dallas, TX (US)

(72) Inventor: Daniel A. Worrel, Dallas, TX (US)

(73) Assignee: SUREMKA, LLC, Dallas, TX (US)

( * ) Notice: Subject to any disclaimer, the term of this patent is extended or adjusted under 35 U.S.C. 154(b) by 292 days.

(21) Appl. No.: 18/078,324

(22) Filed: Dec. 9, 2022

(65) Prior Publication Data

US 2023/0115451 A1    Apr. 13, 2023

Related U.S. Application Data

(63) Continuation-in-part of application No. 16/779,584, filed on Feb. 1, 2020, now Pat. No. 11,607,322.

(Continued)

(51) Int. Cl.
*A61F 2/46* (2006.01)
*A61B 17/16* (2006.01)
(Continued)

(52) U.S. Cl.
CPC ........ *A61F 2/4601* (2013.01); *A61B 17/1635* (2013.01); *A61B 17/1714* (2013.01);
(Continued)

(58) Field of Classification Search
CPC .......... A61F 13/15707; A61F 13/15715; A61F 13/15747; A61F 13/2088; A61F 13/2082; A61F 2/4601; A61F 2/08; A61F 2/0805; A61F 2/95; A61F 2/82; A61F 2/07; A61F 2/2846; A61F 2/46; A61F 2/4644; A61F 2/2415; A61F 2/2418; A61F 2240/001; A61F 2002/4622; A61F 2002/072; A61F 2002/075; A61F 2002/077; A61F 2002/2835; A61F 2002/30688; A61F 2002/5093; A61F 2002/5095; A61F 2002/0841; A61F 17/1635; A61F 17/04;
(Continued)

(56) References Cited

U.S. PATENT DOCUMENTS

2001/0030269 A1* 10/2001 Evans ................... F21V 23/06
248/231.51
2003/0172504 A1* 9/2003 Sageser ............... A61F 13/2085
28/118

OTHER PUBLICATIONS

Amazon.com: Fox Shox Fork Shaft clamps, all RC2 forks—803-00-830: Sports & outdoors. (n.d.). https://www.amazon.com/Fox-Shox-Shaft-Clamps-Forks/dp/B08JQPP62Y, accessed Nov. 22, 2024 (Year: 2009).*

* cited by examiner

*Primary Examiner* — Marcela I. Shirsat

(57) ABSTRACT

A graft compression system for compressing soft tissue grafts used in connection with reconstructive surgery. The graft compression system includes an upper press body and lower press body, pivotally couple to one another, each having inner sides having a plurality of parallel semi-circular shaped channels formed thereon. The plurality of parallel semi-circular shaped channels have sequentially decreasing channel widths. The upper press body and said lower press body of the graft compression system are configured to pivot about a pivot pin such that the inner sides abut one another, and such that the two sets of semi-circular shaped channels are substantially aligned with one another so as to receive a graft for compression. A screw press barrel is attached to the lower press body, on a side opposite the pivot pin, and is configured to compress the upper press body and lower press body.

4 Claims, 32 Drawing Sheets

Related U.S. Application Data

(60) Provisional application No. 63/422,816, filed on Nov. 4, 2022, provisional application No. 63/287,878, filed on Dec. 9, 2021, provisional application No. 62/800,134, filed on Feb. 1, 2019.

(51) Int. Cl.
*A61B 17/17* (2006.01)
*A61F 2/08* (2006.01)
*A61F 2/24* (2006.01)
*A61F 2/28* (2006.01)
*A61F 2/50* (2006.01)
*A61F 2/95* (2013.01)
*A61F 13/15* (2006.01)
*A61L 27/36* (2006.01)
*B29C 43/00* (2006.01)
*B29C 43/04* (2006.01)
*B29C 43/14* (2006.01)
*B29C 43/18* (2006.01)
*B29C 43/36* (2006.01)

(52) U.S. Cl.
CPC ........... *A61F 2/0805* (2013.01); *A61F 2/0811* (2013.01); *A61F 2/2433* (2013.01); *A61F 2002/2835* (2013.01); *A61F 2002/5093* (2013.01); *A61F 2/9524* (2020.05); *A61F 2/9526* (2020.05); *A61F 13/15707* (2013.01); *A61F 13/15747* (2013.01); *A61L 27/3662* (2013.01); *B29C 43/006* (2013.01); *B29C 43/04* (2013.01); *B29C 2043/147* (2013.01); *B29C 43/184* (2013.01); *B29C 2043/3602* (2013.01)

(58) Field of Classification Search
CPC ............. A61F 17/0401; A61F 17/1714; A61B 5/4533; A61B 5/4523; A61B 17/1635; A61B 17/04; A61B 17/0401; A61B 17/1714; B29C 43/003; B29C 43/00; B29C 43/006; B29C 43/02; B29C 43/021; B29C 43/027; B29C 43/04; B29C 43/10; B29C 43/102; B29C 43/14; B29C 43/18; B29C 43/184; B29C 43/34; B29C 43/36; B29C 2043/028; B29C 2043/029; B29C 2043/141; B29C 2043/147; B29C 2043/148; B29C 2043/181; B29C 2043/182; B29C 2043/3411; B29C 2043/3602; F21V 21/08; F21V 21/088
USPC .......... 28/118, 116; 264/324, 299, 320, 325; 604/385.17, 904
See application file for complete search history.

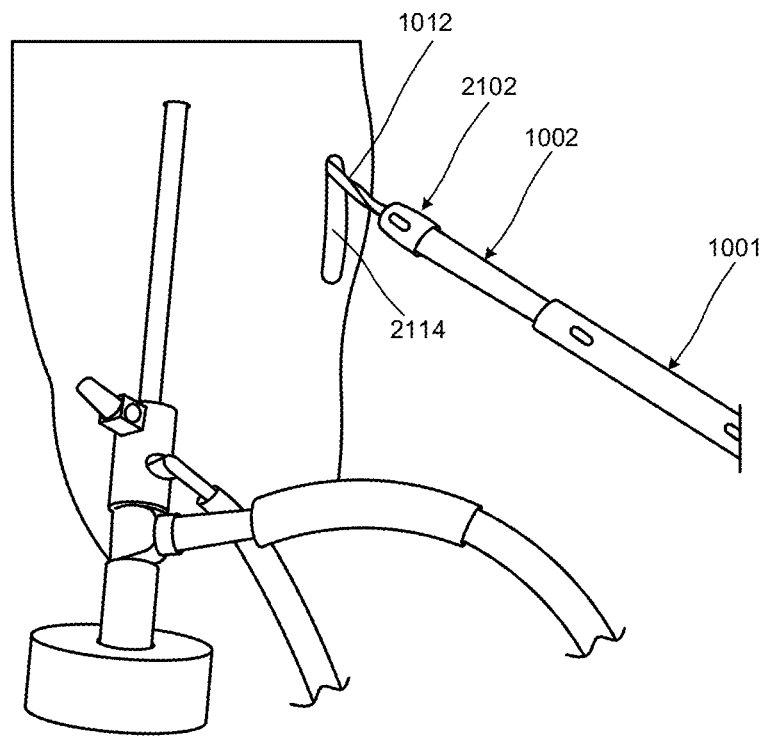
FIG. 21A
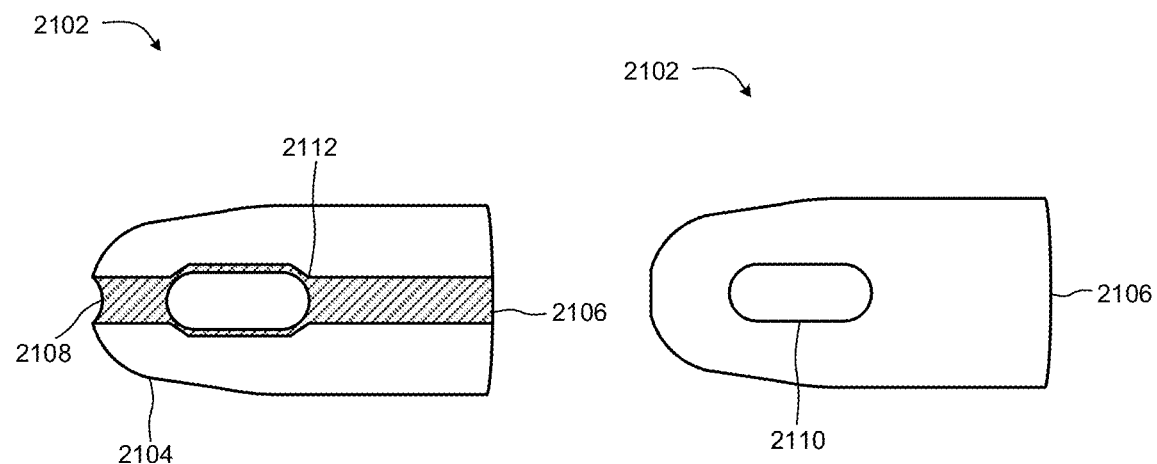
FIG. 21B
FIG. 21C

GRAFT COMPRESSION SYSTEM

BACKGROUND OF THE INVENTION

1. Field of the Invention

The present invention relates generally to systems and devices for use in conjunction with surgical techniques, and more specifically, to a graft compression system and tools utilized for compressing soft tissue grafts used in connection with reconstructive surgery on the anterior cruciate ligament (ACL), posterior cruciate ligament (PCL), other ligaments, as well as various other types of surgical procedures and applications involving the use of grafts on other various parts of human and animal bodies.

2. Description of Related Art Including Information Disclosed Under 37 CFR 1.97 and 1.98

The anterior cruciate ligament (ACL) is one of four main ligaments of the human knee. The ACL works to resist, among other things, anterior tibial translation and rotational loads on the knee. This function prevents anterior tibial subluxation of the lateral and medial tibiofemoral compartments that accounts for what is known the "pivot-shift phenomena." An ACL tear is one of the most common knee injuries, with over 100,000 ACL tears occurring in the U.S. annually. When an ACL tear occurs, most patients will require ACL reconstruction surgery, which generally involves the removal of the torn or ruptured ACL, and the replacement with a piece of tendon or ligament from the patient or from a donor. Other ligaments, such as the posterior cruciate ligament (PCL), may also be torn, which requires PCL reconstruction surgery.

Traditional ACL and PCL surgery typically involves the preparation of a soft-tissue tendon graft having a particular diameter, which is positioned within a bone tunnel drilled by the surgeon, the bone tunnel typically sized to have a diameter approximately equal to the diameter of the graft. The graft is then secured to the patient's bones with screws or other fixation devices such as buttons. The graft will then serve as scaffolding on which new ligament tissue can grow. Drawbacks to traditional ACL and PCL reconstruction surgical techniques include the increased occurrence of less than optimal healing environments and tissue recovery, as well as increased micro-motion between the graft and bone, which stimulates the formation of a fibrous, mechanically inferior scar. These complications can result in more tissue trauma, increased swelling, more pain for the patient, and slower rehabilitation. Such complications arising from traditional ACL and PCL surgery, as outlined above, can be caused by the significant volume of the bone tunnel drilled by the surgeon. Occurrences of graft failure following traditional ACL or PCL surgery is also known to sometimes arise from surgeons utilizing traditional methods of graft fixation.

What is needed is a system for compressing soft tissue tendon grafts that can be easily sterilized prior to surgery, and manually operated by surgeons and/or other operating room personnel to prepare grafts having substantially reduced diameters for use in both traditional and less invasive ACL reconstruction surgery (including "All Inside" ACL surgery), PCL reconstruction surgery, and surgeries involving other ligaments or procedures requiring the compression of grafts. Soft tissue grafts having substantially reduced diameters, with volumes reduced by 50% or more, will in turn allow for the substantial reduction in the volume of bone tunnels/sockets that must be drilled during surgery (resulting in less trauma to the patient, pain, and swelling). The compression of soft tissue tendon grafts will also allow, once the graft rehydrates, for the creation of a biologic compressive fit. This biologic compressive fit will minimize micro-motion, assist in tissue recovery, and improve the healing environment. The creation of a biologic compressive fit will also make it unnecessary for surgeons to use interference screws and buttons to affix the graft (leading to fewer complications of the type outlined above). What is also needed are compression tubes to facilitate the compression and surgical placement of compressed grafts. What is also needed are instruments and tools for the compression and placement of grafts. The graft compression system, instruments, and tools disclosed herein satisfies these needs and others as will become apparent to one of ordinary skill after a careful study of the detailed description and embodiments.

BRIEF DESCRIPTION OF THE SEVERAL VIEWS OF THE DRAWINGS

The present invention will be more fully understood by reference to the following detailed description of the preferred embodiments of the present invention when read in conjunction with the accompanying drawings, wherein:

FIG. 21A is perspective view of a hollow insertion cap (2102) mounted on a proximal end of the embodiment of the elongate compression tube (with compressed surgical graft within) as depicted in FIG. 14, ready for insertion into an incision in a patient;

FIG. 21B is a first side view of a hollow insertion cap (2102) for mounting on a proximal end of an embodiment of the elongate compression tube (with compressed surgical graft within) as depicted in FIG. 21A;

FIG. 21C is a second opposing side view of the hollow insertion cap (2102) depicted in FIG. 21B, for mounting on a proximal end of an embodiment of the elongate compression tube (with compressed surgical graft within) as depicted in FIG. 21A;

Figure 1:
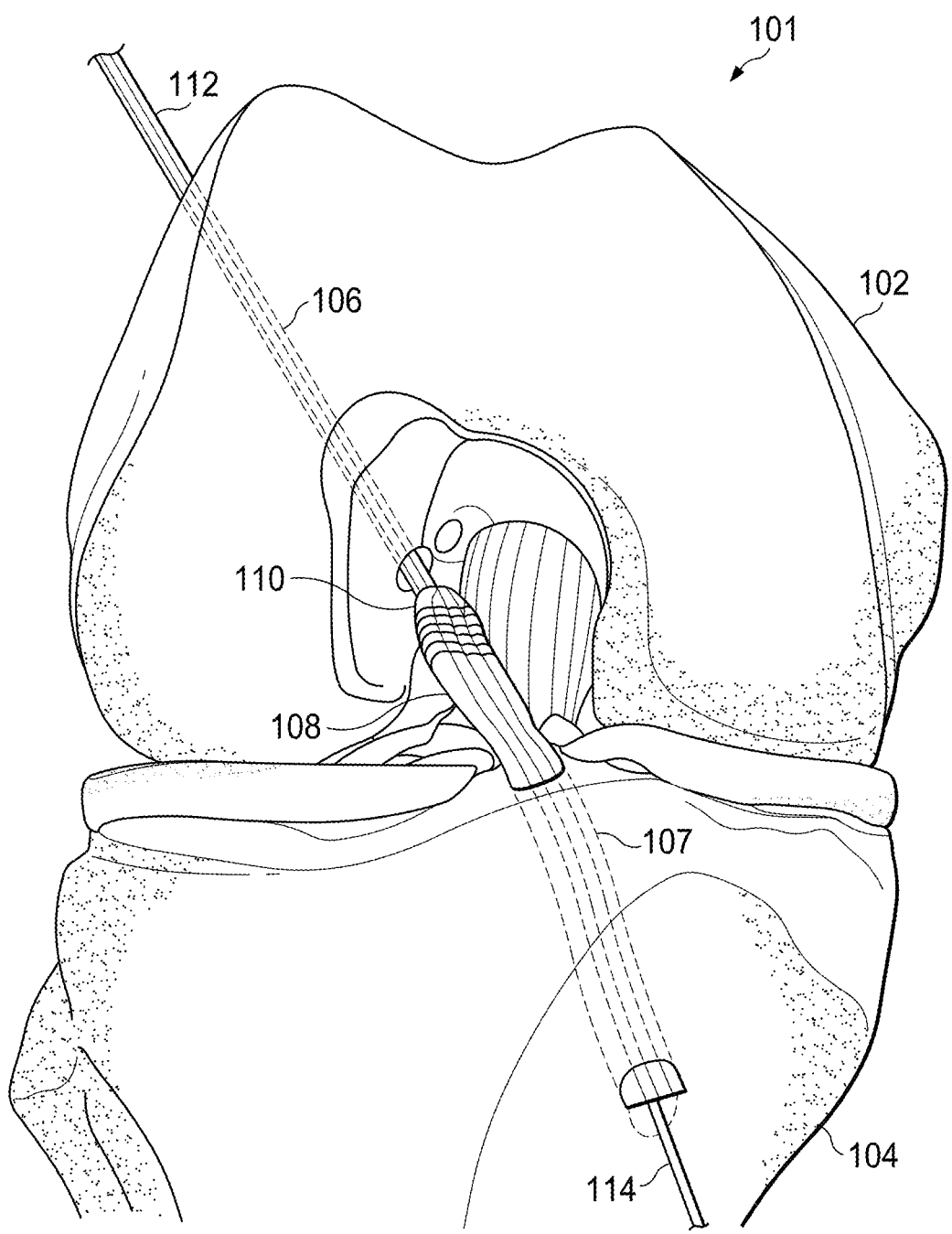
FIG. 1 is a front cut-away view of the surgical placement of a prior art soft tissue graft within a femoral tunnel and tibial tunnel of a patient during ACL reconstruction surgery.

The above figures are provided for the purpose of illustration and description only, and are not intended to define the limits of the disclosed invention. Use of the same reference number in multiple figures is intended to designate the same or similar parts. Furthermore, if and when the terms "top," "bottom," "first," "second," "upper," "lower," "height," "width," "length," "end," "side," "horizontal," "vertical," and similar terms are used herein, it should be understood that these terms have reference only to the structure shown in the drawings and are utilized only to facilitate describing the particular embodiment. The extension of the figures with respect to number, position, relationship, and dimensions of the parts to form the preferred embodiment will be explained or will be within the skill of the art after the following teachings of the present invention have been read and understood.

DETAILED DESCRIPTION OF THE EMBODIMENTS

Several exemplary embodiments of the graft compression system will now be described with reference to the drawings. Unless otherwise noted, like elements will be identified by identical numbers throughout all figures. The invention(s) illustratively disclosed herein suitably may be practiced in the absence of any element that is not specifically disclosed herein.

Systems and other devices useable for surgical soft tissue graft compression, as well as methods for use of such systems/devices, are disclosed herein. It should be noted that while the exemplary embodiments of the invention described herein are associated with ACL reconstruction surgery, the graft compression systems and methods taught below are not limited to such uses, but could also be equally utilized in connection with the surgical reconstruction of the posterior cruciate ligament (PCL) and other ligaments, as well as various other types of surgical procedures and applications involving the use of grafts on other various parts of human and animal bodies.

Referring now to FIG. 1, a front cut-away view of the surgical placement of a prior art graft (108) within a femoral tunnel (106) and tibial tunnel (107) of a patient during ACL reconstruction surgery is depicted. As noted above, traditional ACL surgery typically involves the preparation of a soft-tissue tendon graft having a particular diameter, which is positioned within a bone tunnel or tunnels drilled by the surgeon. The bone tunnel(s) are typically sized to have a diameter approximately equal to the diameter of the graft. Accordingly, a reduction of the size of the diameter of the graft will allow tunnels of reduced diameter to be utilized, resulting in less trauma to the patient and quicker recovery times.

The goal of ACL surgery is to restore stability to the injured knee. Grafts used in ACL surgery act as a scaffolding on which new ligament tissue may grow. One example of a type of ACL surgical graft is a patellar tendon autograft that utilizes the patient's own tendon to replace the torn ACL. Other types of ACL surgical grafts include, but are not limited to, hamstring tendons, quadriceps tendons, and cadaver tendons. When preparing an ACL surgical graft prior to surgery, surgical sutures (110) are often tied to the two ends of the graft such that, during positioning of the grant during surgery, a first length of suture line (112) is attached to one end of the graft and extends through the femoral tunnel (106), and a second length of suture line (114) is attached to the other end of the graft and extends through the tibial tunnel (107). Suture lines attached to the ends of the surgical graft allow surgeons to physically manipulate the movement and positioning of the surgical graft via the application of pulling forces on the suture lines.

Figure 2:
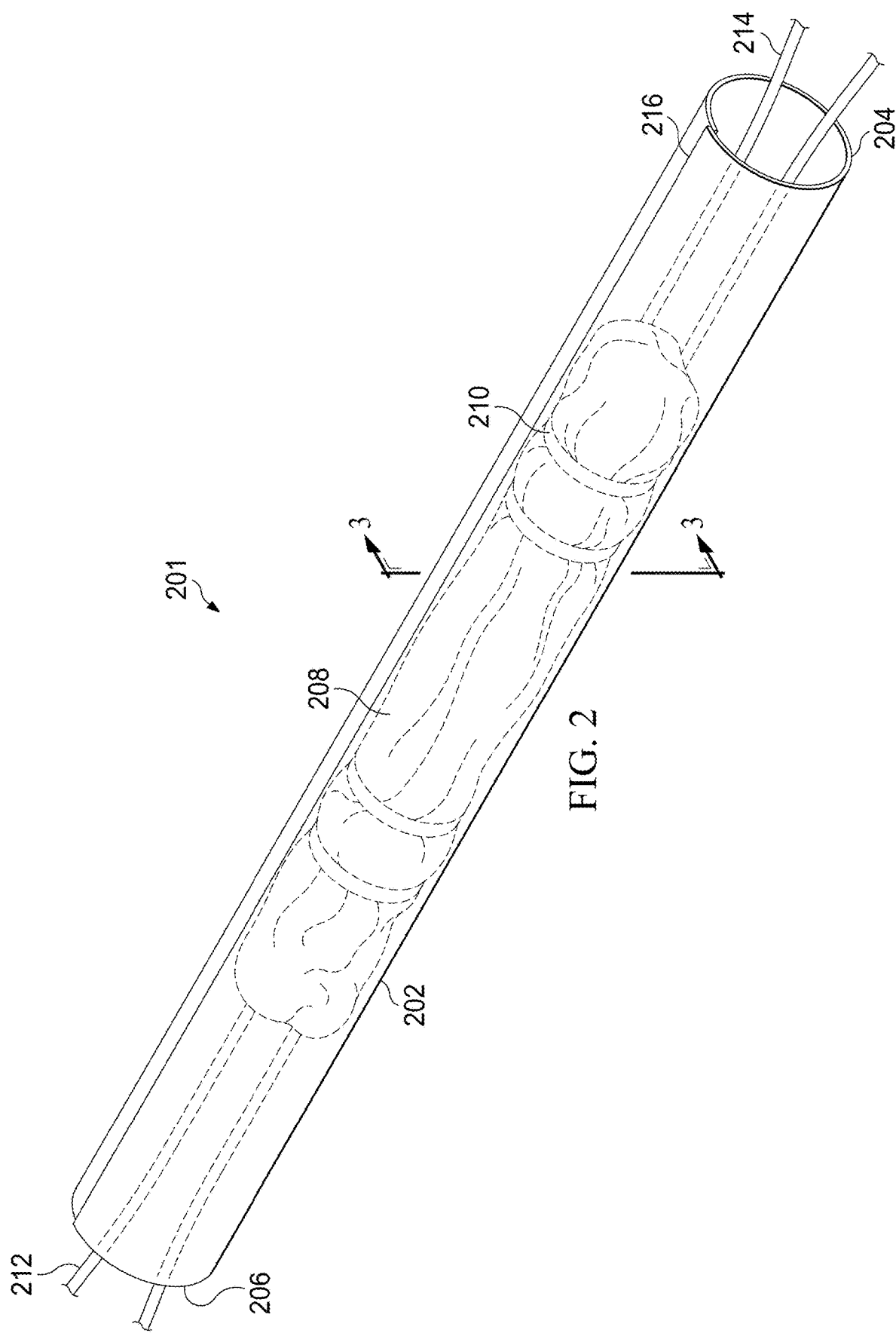
FIG. 2 is a perspective view of one embodiment of an elongate compression tube of the graft compression system, said compression tube having a surgical graft temporarily located within said tube for compression.

Referring now to FIG. 2, depicted is a perspective view of one embodiment of a compression tube (202) of the graft compression system, said compression tube having a surgical graft (208) temporarily located within said tube for compression prior to removal from the tube and placement in a patient during ACL reconstructive surgery or another surgery requiring compression of a graft or other soft tissue element. It is contemplated that surgical grafts commonly used in ACL reconstructive surgery may be used in conjunction with the graft compression system taught herein. In one embodiment, the compression tube (202) is substantially cylindrical in appearance and has substantially cylindrical walls forming a hollow lumen in which a surgical graft may be inserted through openings of the ends of the compression tube. Openings are formed on opposing ends (204, 206) of the compression tube, allowing for the insertion and removal of a surgical graft. Suture lines (212, 214) may be tied or otherwise attached (210) to respective portions of the surgical graft (208). The suture lines (212, 214) aid in maintaining the compactness of the graft, and also provide a means by which the graft may be physically moved and/or otherwise manipulated via pulling forces applied by a surgeon to the suture lines.

In one embodiment, distally oriented suture lines (212) attached to a graft may be "threaded" by a surgeon through the lumen of the compression tube until they emerge through the distal end (206) of said compression tube. The distally oriented suture lines (212) may then be pulled such that the graft is inserted into the compression tube so that the entire graft is enclosed within said compression tube as shown in FIG. 2.

In one embodiment, the elongate compression tube (202) shaft is constructed of a shape memory alloy such as Nitinol that may be "trained" to naturally compress to a predetermined inner diameter. In other embodiments, the compression tube may be constructed of other materials such as stainless steel, aluminum, and other various alloys and polymers that are rigid enough to maintain their overall cylindrical form, yet flexible enough to be compressed with respect to the inside diameter of the lumen of the compression tube and maintain such compression to an acceptable degree. The ability of the compression tube to expand and compress the diameter of the lumen of the tube is provided by the structure of the tube including a discontinuity or gap (216) in the wall of the tube such that when the tube is in an expanded state (not shown), the discontinuity or gap in the tube wall is more readily visible. In other words, while the compression tube appears to be substantially cylindrical in appearance, the tube wall that forms the lumen of the tube is not an uninterrupted wall around the entire circumference of the tube, but rather comprised of a first longitudinal side of a tube wall and a second longitudinal side of a tube wall that are not connected to one another, leaving a gap (216) in the tube wall. When the compression tube is compressed, the first longitudinal side of a tube wall overlaps and can slide over a second longitudinal side of a tube wall as depicted at FIG. 2 at 216, thereby effectively decreasing the inner diameter of the lumen of the compression tube (the outer diameter of the compression tube is also decreased). When a first longitudinal side of a tube wall overlaps a second longitudinal side of a tube wall (or alternatively, can slide underneath the other tube wall), there is the appearance of a line running down the longitudinal length of the compression tube where there is a discontinuity or gap in the tube wall. It is contemplated that water and other substances having lubricating properties can be applied to the outer and/or inner tube walls to aid in the ability of the tube to be compressed.

In one embodiment, a tool (not shown) configured and sized to insert into the gap of the compression tube, may be inserted into such gap. Such tool may be tapered such that as the tool is inserted into the tube gap (216), the diameter of the tube will increase, the tube being constructed of flexible material. By using the tool to increase the diameter of the compression tube, a graft having a diameter larger than the inside diameter of the unaltered compression tube (before insertion of tool into the gap) may be inserted into such compression tube. Once a graft is inserted into the compression tube, the compressive properties of the shape memory alloy (such as Nitinol) or other material used to construct the tube, will act to compress the graft. Thus, the compression tube may act as a first stage of compression of the graft. By inserting the compression tube (and graft enclosed within) into the other components of the graft compression system as discussed below, even further compression of the graft will occur.

Figure 3:
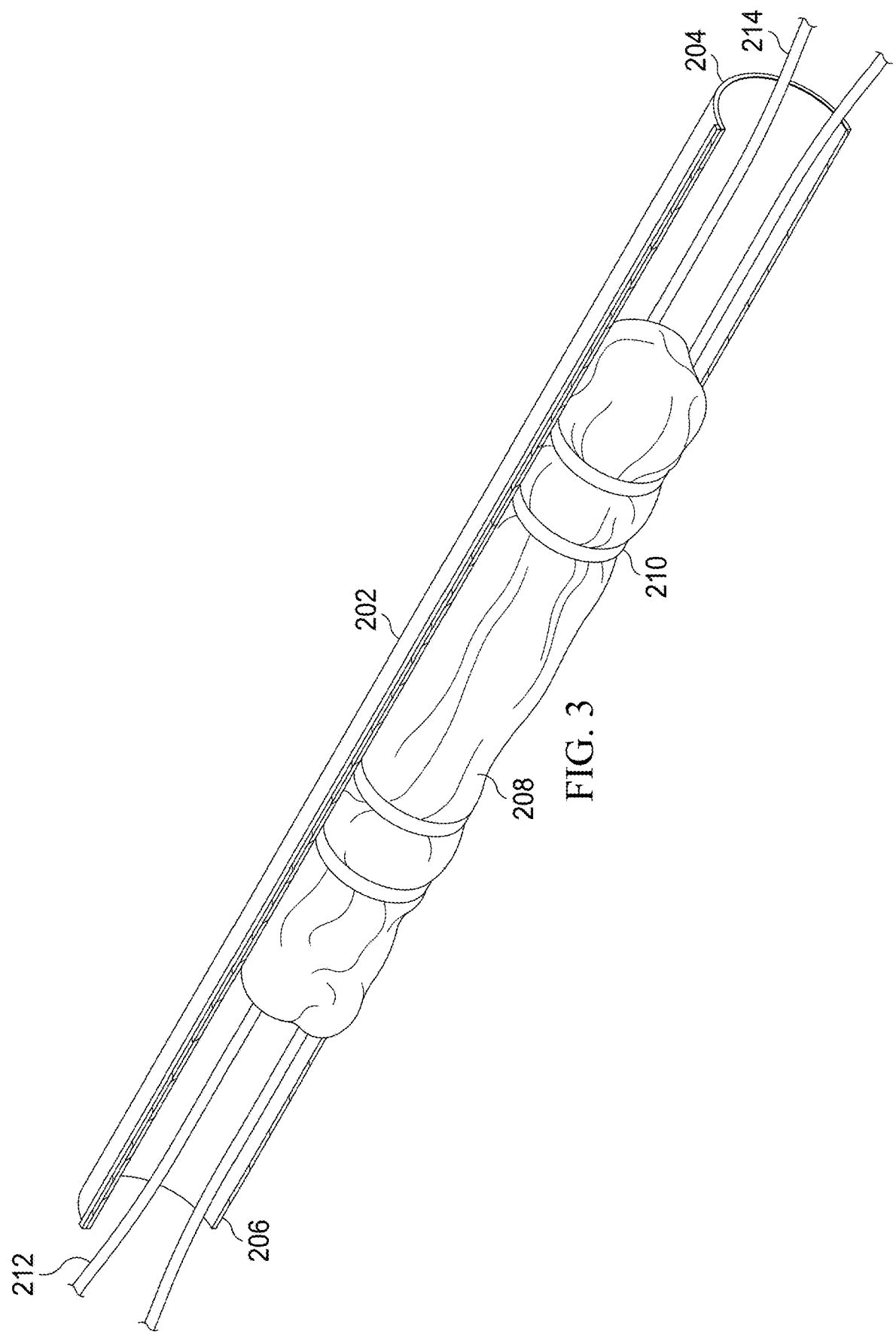
FIG. 3 is a perspective cutaway view of the embodiment of the expandable and compressible elongate compression tube and surgical graft depicted in FIG. 2.

Referring now to FIG. 3, a perspective cutaway view of the embodiment of the compression tube and surgical graft depicted in FIG. 2 is depicted. It should be noted that the length of the graft appearing (208) in FIGS. 2 and 3, as compared to the length of the compression tube (202), is merely intended to illustrate the overall structures of the graft compression system and the relationships between the components thereof. Ideally, a compression tube will have a length selected to be the same length or a larger length as the length of the graft to be compressed within the compression tube. In one embodiment, the length of the compression tube is 120 millimeters. However, in alternate embodiments, the compression tube may have various longer or shorter lengths to accommodate grafts having various lengths used for ACL reconstructive surgery and other types of surgeries. Moreover, the graft compression system taught herein may be utilized regardless of the length differential between the surgical graft to be compressed and the compression tube utilized in compressing such graft. Likewise, the diameter of the compression tube in an uncompressed state will ideally be roughly the same diameter as the diameter of the uncompressed graft to be compressed. Although, as discussed above, it is contemplated that in some embodiments, the compression tube may have a smaller diameter than the uncompressed graft and the compression tube will be at least temporarily expanded to allow the graft to be inserted within. It is also contemplated that in some embodiments of the graft compression system, a funnel type device could be utilized in conjunction with the system to aid in inserting a graft into an end of a compression tube that has a diameter smaller than a surgical graft to be inserted. It is contemplated that water and other substances having lubricating properties can be utilized, in conjunction with suture lines, to assist in the insertion of the graft into the compression tube. In some alternate embodiments of the compression tube, edges of the tube formed on one or both of the ends (204, 206) of the tube may be modified to present a blunter edge or other structure so as to decrease the chance that a graft might be damaged when inserting the graft into the compression tube. Indeed, a protective polymer ring may be inserted over such edge or edges at the ends of the compression tube to protect the graft as it is inserted into the compression tube, the ring(s) being removable prior to insertion of the compression tube into other components of the graft compression system.

Figure 4:
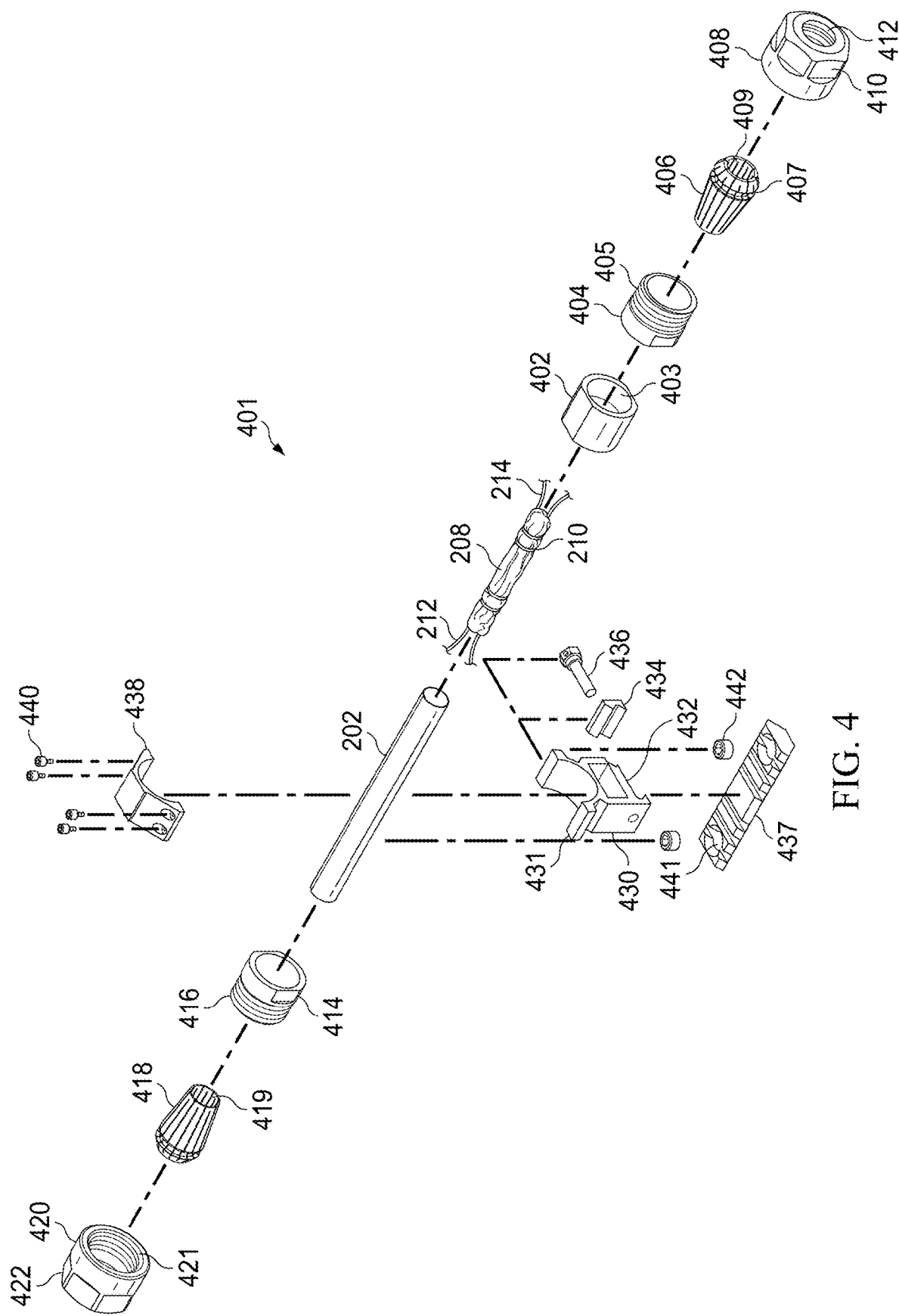
FIG. 4 is an exploded view of one embodiment of the graft compression system.
Figure 6:
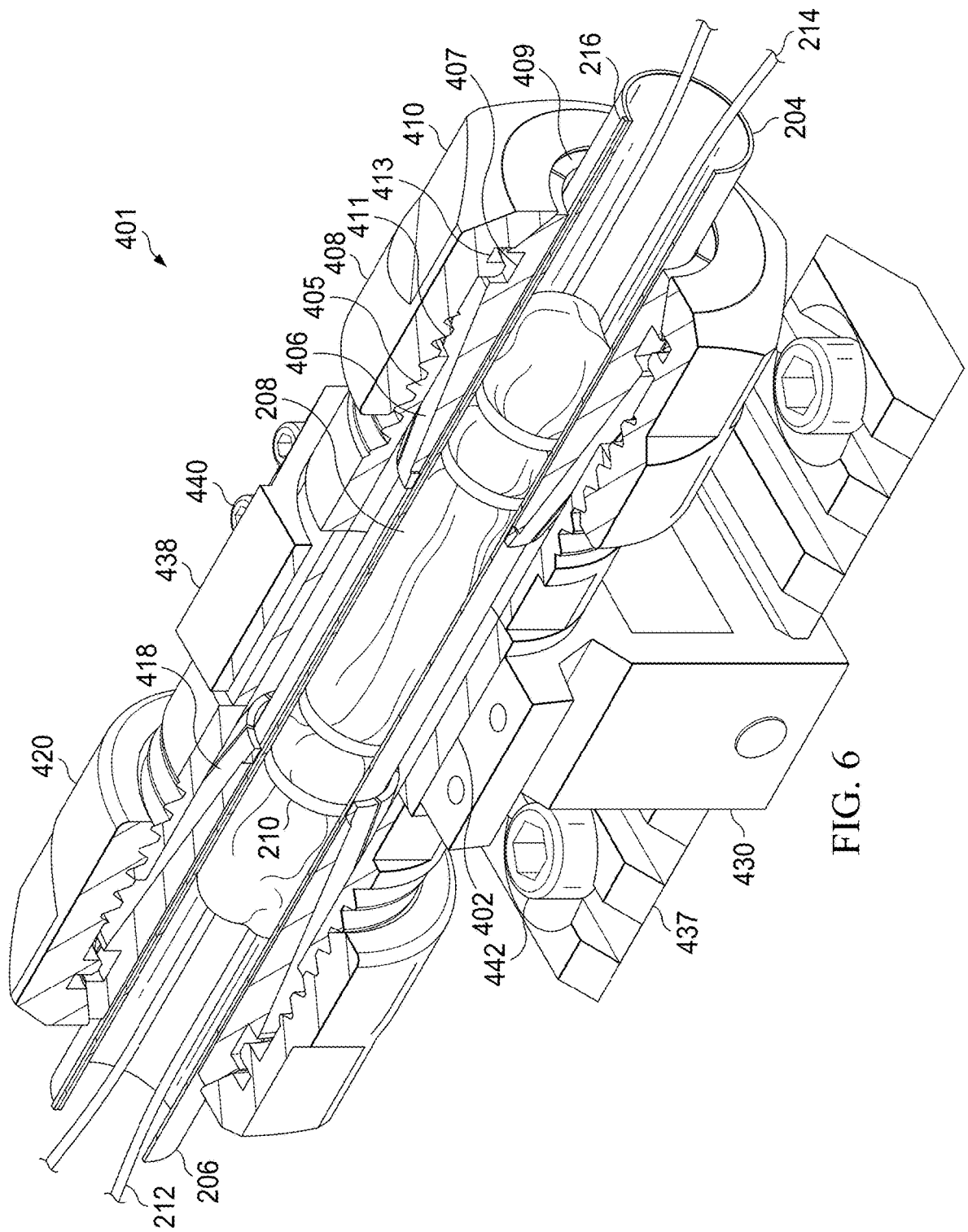
FIG. 6 is a cutaway perspective view of the embodiment of the graft compression system depicted in FIG. 5.

Referring now to FIG. 4, an exploded view of one embodiment of the graft compression system (401) is depicted. In one embodiment, a soft tissue tendon graft (208) may be folded to an appropriate size prior to the initiation of a compression sequence utilizing the graft compression system taught herein. Surgical suture line (212, 214) may be affixed (210) to one or both ends of the graft, and used to insert the graft into the compression tube (202) as described above. In one embodiment of the graft compression system, a compression chamber housing comprising a hollow shaft with an inner diameter greater than an outer diameter of the compression tube, is sized for the insertion of the compression tube within. In one embodiment, the compression chamber housing may be comprised of a first proximal hollow shaft body (404) and a second distal hollow shaft body (414) that are removably fastened or permanently affixed to opposing ends of an intermediary hollow shaft body (402). When attached or affixed to one another, the first proximal hollow shaft body (404), and intermediary hollow shaft body (402) form a continuous lumen into which the compression tube may be inserted as shown in FIG. 6. While the first proximal hollow shaft body (404), second distal hollow shaft body (414), and intermediary hollow shaft body (402) are shown to be three separate bodies in FIG. 4, it is contemplated that a single hollow body may serve the function of a compression chamber sized for the insertion of a compression tube in alternate embodiments of the graft compression system.

In one embodiment, the outer surface of the first proximal hollow shaft body is threaded (405) to mate with correspondingly sized threads (411) formed on the inner wall of the proximal collet nut (408) as depicted in FIG. 6. On the distal side of the graft compression system, the second distal hollow shaft body (414) has threads (416) formed on an outer surface thereof that are configured to mate with correspondingly sized threads formed on the inner wall of the distal collet nut (420) as depicted in FIG. 6. By tightening the proximal collet nut on the first proximal hollow shaft body, an inner collar (413) of the collet nut will engage with a slot (407) formed on the proximal collet (406) to reduce the diameter of the lumen (409) formed within the collet and thereby compress the compression tube (202) and graft positioned (208) within. Similarly, the distal collet nut (420) is likewise configured to threadedly engage the second distal hollow shaft body (414) to compress the inside lumen (419) diameter of the distally positioned collet (418), thereby further compressing the distal end of the compression tube and surgical graft within.

Still referring to FIG. 4, in one embodiment of the graft compression system, the proximal (405), intermediary (402), and distal (414) hollow shaft bodies which together form the compression chamber housing are constructed of metal such as, for example, stainless steel, but may in alternate embodiments may be constructed of other types of metals, alloys, or polymers that are capable of easy sterilization utilizing common sterilization systems employed by hospitals and other surgical centers. Off-the-shelf ER type collets as depicted in FIG. 4 have a tapered outer surface and a substantially cylindrical inside diameter. In the embodiment of the graft compression system depicted in FIG. 4, the collets (406, 418) are configured to be positioned inside the respective ends of the distal and proximal hollow shaft bodies of the compression chamber. The larger diameter ends of said collets are, in the embodiment of the graft compression system shown in FIG. 4, oriented towards the respective ends of graft compression system.

In one embodiment of the graft compression system, a bracket similar to riflescope rings may be used to secure and stabilize the proximal, distal, and intermediary hollow shaft bodies to a rail (437) that may in turn be secured to a working board or other structure located in an operating room or other space designed for preparation of the surgical graft prior to surgery. The stabilizing bracket may in one embodiment comprise an upper semi-circular ring (438) configured to wrap around the top of the intermediary hollow shaft body (402) and be fastened to a lower semi-circular ring (431) configured to cradle the bottom of the said intermediary hollow shaft body. A plurality of screws may be utilized to fasten the upper semi-circular ring (438) to the lower semi-circular ring (431). The lower semi-circular ring (431) may further include lower structures similar to those of riflescope rings, including a slot (432) configured to mate with a rail body (437). An adjustable slot wall (434) configured to abut the slot structure (432) of the lower semi-circular ring (431) may be tightened and loosened using a screw (436), thereby securing the lower semi-circular ring (431) structure to a rail (437), which in turn may be secured to a working board (504) using screws (not shown) and nuts (442) as depicted in FIG. 5.

Figure 5:
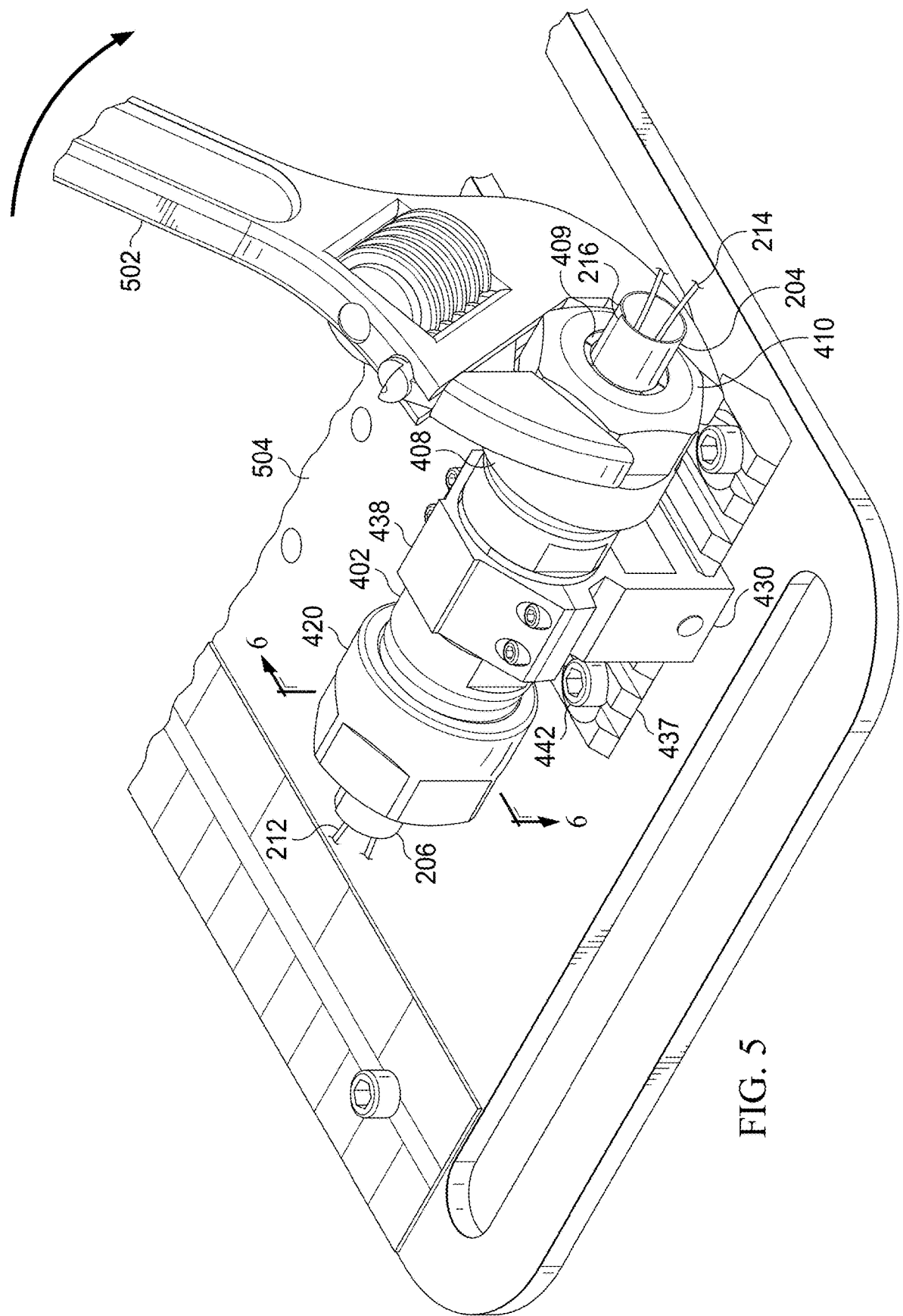
FIG. 5 is a perspective view of the embodiment of the graft compression system depicted in FIG. 4, said system having been mounted on a working board, and further depicting a wrench attached to an outer surface of a first proximal collet nut.

Referring now to FIG. 5, depicting a perspective view of the embodiment of the graft compression system depicted in FIG. 4, said system having been mounted on a working board (504), and further depicting a wrench (502) attached to an outer surface of a first distal collet nut. The wrench is configured to grasp the hexagonal surfaces (410, 422) of the respective collet nuts such that wrench might turn said collet nuts to tighten or loosen the collets. In one embodiment of the graft compression system, the collet nuts (408, 420) are sized and structurally configured to mate with a respective distal or proximal hollow shaft body to which it is attached. Each of the proximal and distal collets is nested within a respective proximal and distal hollow shaft body. An internal collar protrusion (FIG. 6 at 413 showing internal collar protrusion on proximal collet nut) formed on each collar nut is configured to engage a respective adjacent collet slot (FIG. 6. at 407 showing collar slot on proximal collet). When rotated by a user using a wrench or other tool, the collet nut works to selectively adjust the working inside diameter of the collet. Each collet has an opening on each end of the collet such that, when two or more collets are aligned within the hollow shaft bodies of the graft compression system as described herein, a passageway is formed through the system, allowing for the insertion and removal of a compression tube configured to hold soft tissue grafts. In one embodiment, an ER type collet having a particularly sized inner diameter (for example, a 10 millimeter inside diameter) that is optimized for a graft of a particular size, or selected for a particular type of surgery or particularly sized bone tunnel or socket. Typical collets are capable of inside diameter compression of 1-2 millimeters.

Still referring to FIG. 5, a wrench (502) or similar instrument may be utilized to rotate each collet nut (408, 420) in a counterclockwise direction providing for the closing or tightening of the respective collet to which it is mated. As the collet nut is rotated, the collet's inside diameter will decrease, resulting in the compression of the graft. A collet nut may be rotated in a counterclockwise direction if it is desired to expand the inside diameter of the lumen of the respective collet. Users of the graft compression system will ideally wait for a predetermined period of time (for example, five minutes) prior to removal of the compression tube from the graft compression system. Such a waiting period will aid in preventing the graft from experiencing premature expansion. While ER type collets have been described herein as one type of compressive device that may be utilized to provide compressive force along a lumen of the graft compression system, other types of collets and compressive devices may also be utilized to the extent that such compressive devices are capable of providing compressive forces along all or a portion of the length of a compression tube.

While the preferred embodiment of the graft compression system described herein is configured for manual operation, allowing a surgeon to utilize simple, easily sterilized tools (such as a wrench) to operate the system, it is contemplated that alternate embodiments of the graft compression system may allow for the use of power tools having rotary motors to engage the collet nuts or to otherwise actuate other types of compression devices that may be utilized as substitutes for collets.

The graft compression system described and depicted herein provides many advantages in the field of ACL reconstruction surgery and other types of surgeries involving the use of grafts. One advantage realized is that the graft compression system is capable of being easily sterilized as it is composed of relatively simple and easily assembled/disassembled components. Another advantage of the graft compression system is that it is capable of being manually operated by surgeons and other operating room personnel, requiring only the use of simply hand tools to actuate the compression system. Another advantage of the graft compression system is that it is capable of effectively reducing the overall volume of a graft by 50% or more, meaning that surgeons will be able to significantly reduce the size/volume of bone tunnels and sockets. Thus, as a result, patients will experience less tissue trauma, swelling, and pain.

Other advantages of the graft compression system and its ability to effectively reduce the diameter of a graft, arise from the relatively "tight" fit of the graft within the bone tunnel or socket into which it may be inserted. Once inserted, the graft will rehydrate and expand, creating a biologic compressive fit within such bone tunnel or socket. Such a compressive fit will result in a well-fixed graft, making it unnecessary to utilize interference screws and buttons to affix the graft. The nature of the well-fixed graft arising from the use of compressed grafts will also act to minimize micro-motion, thus reducing scarring. Other benefits arising from use of the graft compression device include faster tissue recovery, improved healing environment, and overall improved outcomes.

Referring now to FIG. 6, depicted is a cutaway perspective view of the embodiment of the graft compression system depicted in FIG. 5. As noted above, an internal collar protrusion (413) formed on each collar nut is configured to engage a respective adjacent collet slot (407). As those of ordinary skill in the art will appreciate, a collet nut, when rotated by a user, works to selectively adjust the working inside diameter of the collet (increasing or decreasing the inside diameter of the collet, depending on the direction the collet nut is rotated). The compression tube (202) may be inserted into an opening (409) in the proximal collet (406) or distal collet (418), which leads to a lumen within the hollow shaft bodies (404, 402, 414). It is contemplated that both collet nuts (408, 420) may be tightened such that the respective collets to which they are engaged will compress the compression tube and in turn the surgical graft within such tube. It is also contemplated that one portion of the compression tube may be compressed, and the compression tube incrementally moved down the lumen of the hollow shaft bodies, and compressed at each incremental step such that the entire length of the compression tube (and graft within) may be subjected to more direct compressive forces of the collet(s). By this method of compression, it would be possible to configure an alternate embodiment of the graft compression system to utilize only a single side of the system depicted in FIG. 6—in other words, it would be possible in alternate embodiments to utilize only a single collet nut and collet to incrementally compress a length of a compression tube.

It is further contemplated that the graft compression system taught herein may be used to compress a graft in a single stage of compression, or in multiple stages of compression by using removable collets having progressively smaller inside diameters. For example, in a first stage of compression, collets having inside diameters compressible from a 10-millimeter diameter to a 9-millimeter diameter may be initially inserted into the respective ends of the hollow shaft bodies. A compression tube containing a surgical graft may be inserted and compressed in the manner described above. Using a tool such as the T-handle collet check (701) described in connection with FIG. 7 below, the compression tube may be removed and the compression better maintained. The first set of collets may then be removed and a second set of collets compressible from a 9-millimeter inside diameter to an 8-millimeter diameter may be inserted into the graft compression system and the compression tube reinserted into the graft compression tube for a second stage of compression. In this manner, the graft compression system may be used to progressively compress a surgical graft in multiple stages prior to use in surgery.

Figure 7:
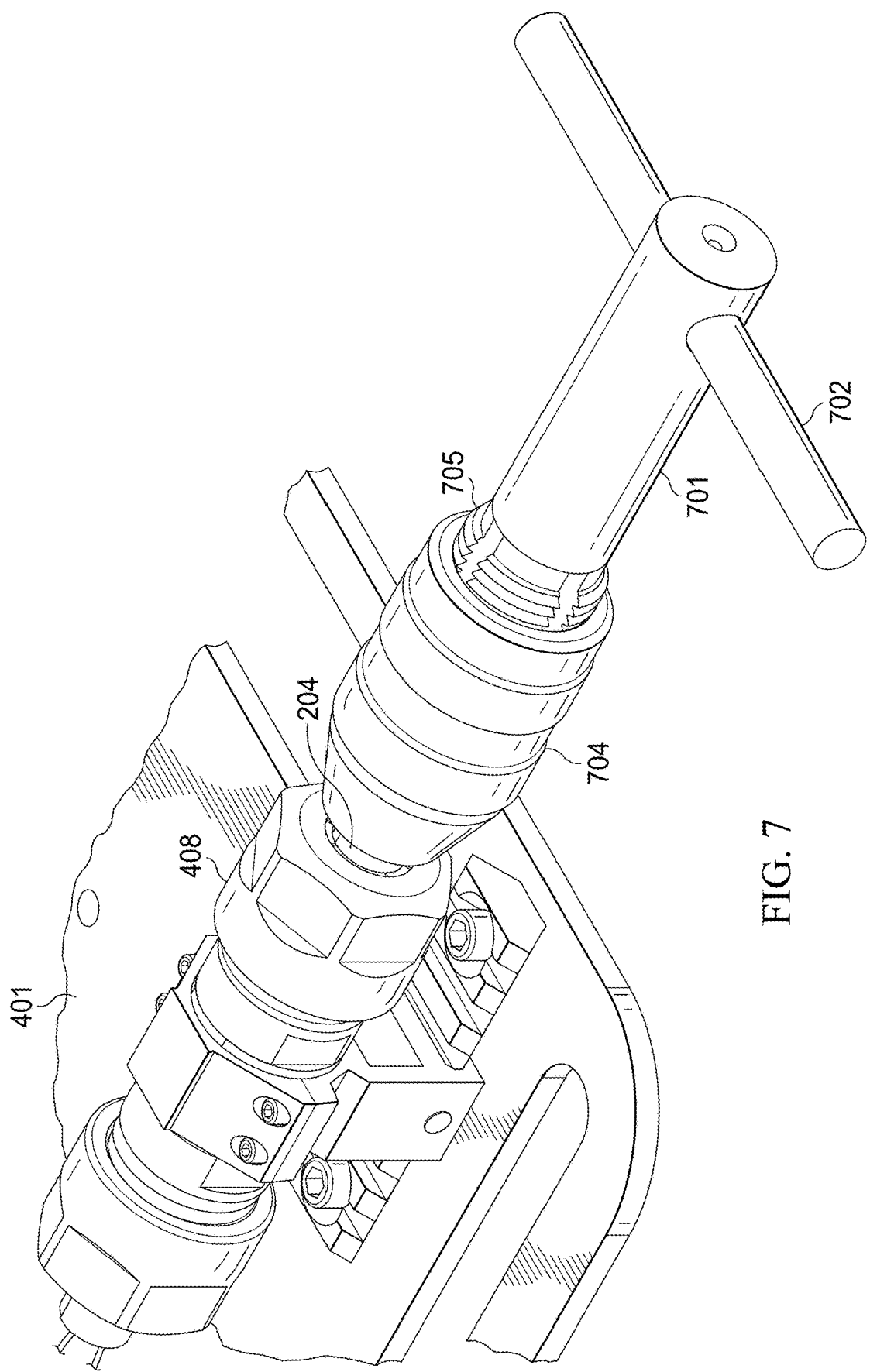
FIG. 7 is a perspective view of the embodiment of the graft compression system depicted in FIG. 5, adjacent to an embodiment of a T-handle collet chuck attached to and maintaining the compression of a proximal end of the expandable and compressible elongate compression tube.

Referring now to FIG. 7, depicted is a perspective view of the embodiment of the graft compression system depicted in FIG. 5, adjacent to an embodiment of a T-handle collet chuck (701) attached to and maintaining the compression of a distal end of the expandable and compressible elongate compression tube. Depending on the materials used to construct the compression tube, it may be necessary to take steps to maintain the compressed diameter of a compression tube after the graft compression system has been used to compress the compression tube and surgical graft within. A T-handle collet chuck having a handle (702) on one end and a threaded chuck (704) for compressing an internal collet (not shown), may be tightly attached around a proximal end (204) of the compression tube such that the diameter of the compression tube does not increase. The collet chuck may then be used to remove the compression tube from the hollow shaft bodies and collets to deliver and insert such compression tube into a surgical cannula or portal holder device, or other type of surgical device being used to place the graft into the surgical site on the patient. Alternatively, such a collet chuck may be used to maintain the compressed diameter of the compression tube, and to remove such compression tube from the graft compression system while a first set of collet devices are removed and a new set of collet devices are inserted in conjunction with a multi-stage compression sequence as described above.

Figure 8:
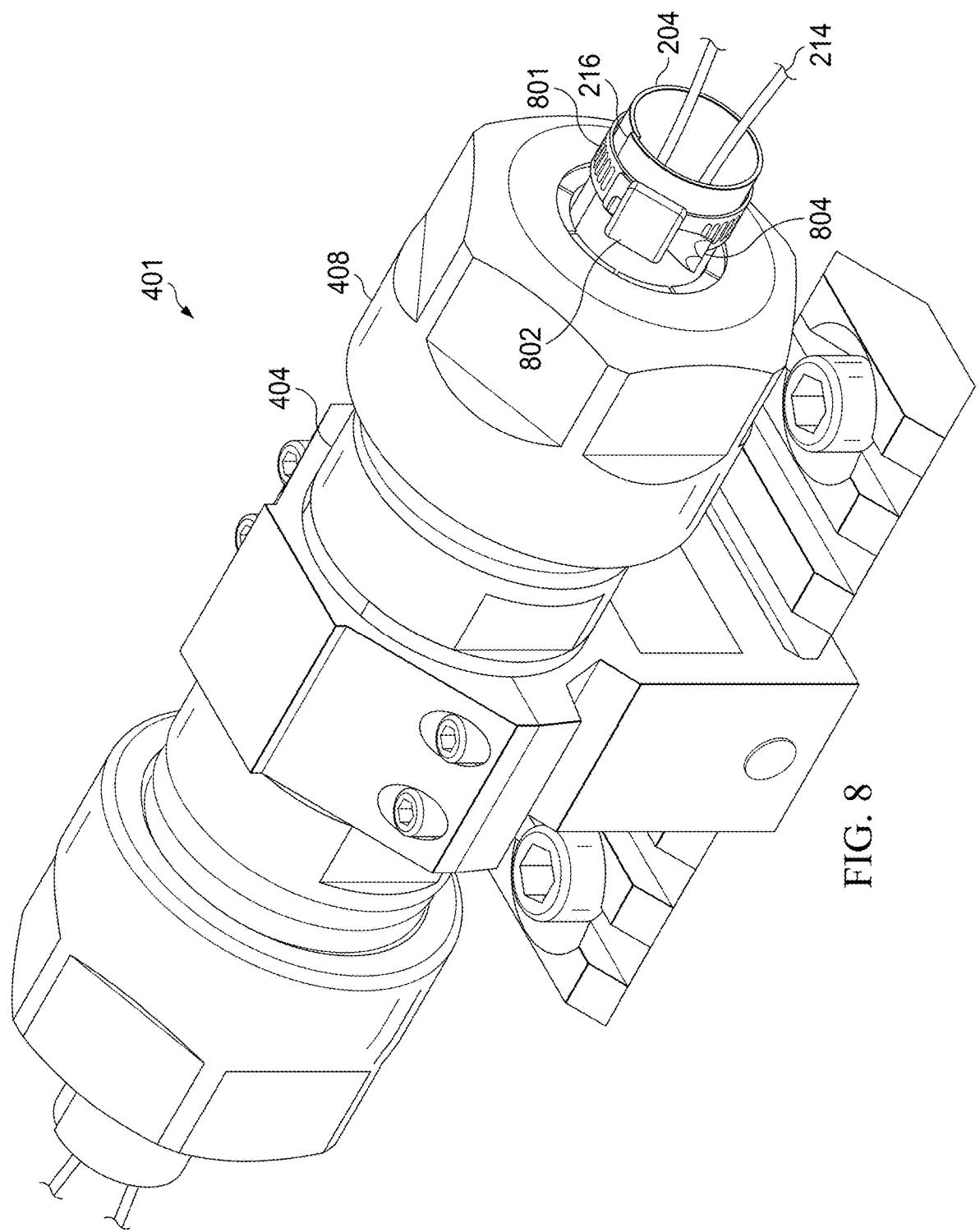
FIG. 8 is a perspective view of the embodiment of the graft compression system depicted in FIG. 5, having an adjustable hose clamp attached to and maintaining the compression of a proximal end of the expandable and compressible elongate compression tube.

Referring now to FIG. 8, depicted is a perspective view of the embodiment of the graft compression system depicted in FIG. 5, having an adjustable hose clamp (801) attached to and maintaining the compression of a proximal end (204) of the expandable and compressible elongate compression tube (202). Once at least a first stage of compression of the compression tube and surgical graft has been completed, an adjustable hose clamp (801) may be tightly fastened to an end of the compression tube using a screw (804) and nut (802) of the clamp such that the diameter of the compression tube does not increase when the tube is removed from the graft compression system. The compression tube may then be removed from the graft compression system, with additional hose clamps fastened along the length of the compression tube. The hose clamp(s) may be used to maintain the compressed diameter of the compression tube until such time as the compression tube may be inserted into a surgical cannula or portal holder device, or other type of surgical device being used to place the graft into the surgical site on the patient. Alternatively, such hose clamp(s) may be used to maintain the compressed diameter of the compression tube while a first set of collet devices are removed and a new set of collet devices are inserted in conjunction with a multi-stage compression sequence as described above. For such a purpose, the hose clamps may be sequentially removed as the compression tube is reinserted into the hollow shaft bodies and collets for the next stage of compression.

Figure 9:
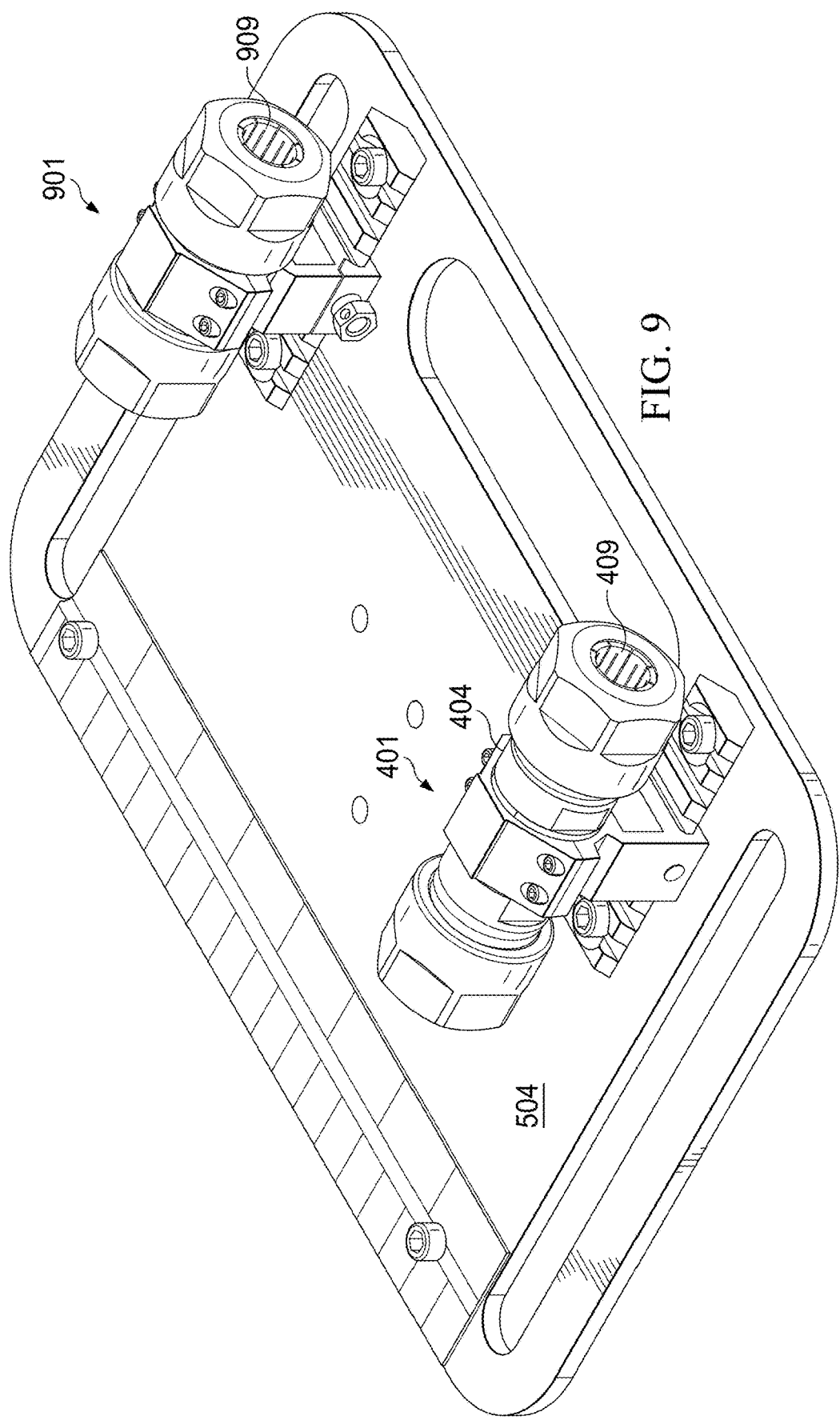
FIG. 9 is a perspective view of the embodiment of the graft compression system depicted in FIG. 5 mounted on a working board adjacent to an alternate embodiment of the graft compression system having a compression shaft with a decreased length.

Referring now to FIG. 9, depicted is a perspective view of the embodiment of the graft compression system that is depicted in FIG. 5, said system being mounted on a working board adjacent to an alternate embodiment of the graft compression system having a compression chamber shaft with a decreased length. By utilizing two or more graft compression devices in close proximity to one another, advantages may be realized in that surgical grafts of various lengths may be compressed without having to make adjustments to the lengths of the hollow shaft bodies. It is contemplated that intermediary hollow shaft bodies having various lengths may be removably fastened to distal and proximal hollow shaft bodies to provide the surgeon with the ability to select an optimal length of a compression chamber. However, in some circumstances, it may be preferable to have ready access to one or more graft compression systems having compression chambers of different lengths immediately available for use without it being necessary to disassemble and reassemble the graft compression system. Another advantage of utilizing multiple graft compression systems in close proximity to one another is that such a configuration gives the surgeon the ability to utilize different sized collets in each graft compression system. In this manner, a surgeon could perform multiple stages of compression without having to disassemble and reassemble graft compression systems to remove and insert progressively smaller collet sets.

In one embodiment, a surgical graft compression system may comprise a compression chamber having an elongate hollow shaft body, said hollow shaft body having a first proximal end and a second distal end, each of said first proximal end and said second distal end having outer surfaces on which threaded surfaces are formed; a proximal first collet nut configured to threadedly fasten to said first proximal end of said elongate hollow shaft body; a distal second collet nut configured to threadedly fasten to said first end of said elongate hollow shaft body; a proximal first collet configured for insertion into said proximal first collet nut; a distal second collet configured for insertion into said distal second collet nut; and a hollow tube having a lumen with a compressible diameter, said hollow tube being configured for removable insertion into said proximal first collet, said compression chamber, and said distal second collet. In another embodiment, said proximal first collet nut includes an internal collar protrusion that is configured to engage a collar slot formed on an outer surface of said proximal first collet. In one embodiment, the counterclockwise rotation of said proximal first collet nut causes an inner collet lumen of said proximal first collet to have decreased diameter. In one embodiment, a first semi-circular upper bracket is fastened to a second semi-circular lower bracket, wherein at least a portion of said compression chamber is secured within said first semi-circular upper bracket and said second semi-circular lower bracket. In one embodiment, said second semi-circular lower bracket is mounted to a board. In another embodiment, a surgical graft compression system may comprise a compression chamber having an elongate hollow shaft body, said hollow shaft body having a first proximal end and a second distal end, said first proximal end having outer surfaces on which threaded surfaces are formed; a collet nut configured to threadedly fasten to said first proximal end of said elongate hollow shaft body; a collet configured for insertion into said collet nut; and a hollow tube having a lumen with a compressible diameter, said hollow tube being configured for removable insertion into said collet and said compression chamber.

Figure 10:
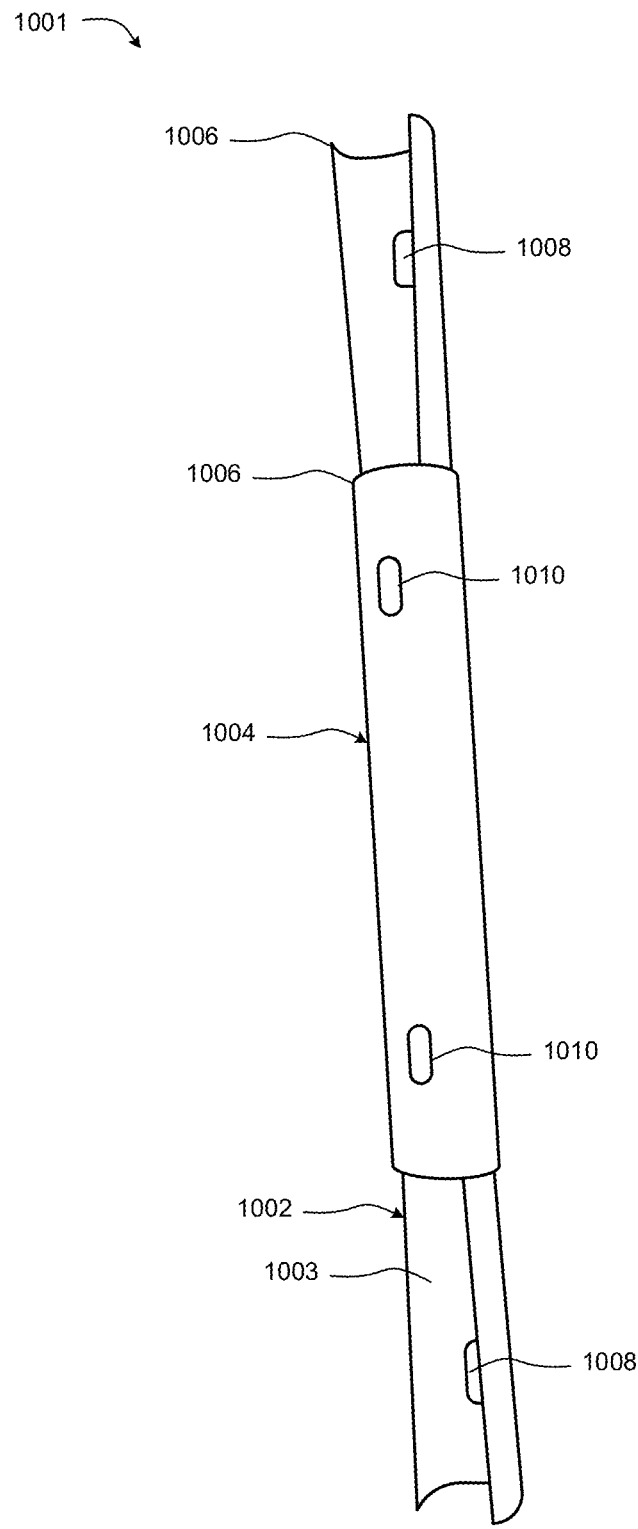
FIG. 10 is a perspective view of an alternate embodiment of an elongate compression tube.

Referring now to FIG. 10, a perspective view of an alternate embodiment of an elongate compression tube (1001) is shown. In one embodiment, the alternate embodiment of an elongate compression tube (1001) includes a first elongate compression shaft (1002) configured to mate with a second elongate compression shaft (1004). In one embodiment, the first elongate compression shaft (1002) has a longer length than the second elongate compression shaft (1004). In one embodiment, the second elongate compression shaft (1004) is configured to have a length substantially equal to a length of a graft prepared to be loaded into the elongate compression tube for compression. As seen in FIG. 10, the second elongate compression shaft has a slightly larger cross-sectional diameter as compared to the first elongate compression shaft, allowing the second elongate compression shaft to mounted on top of the channel (1003) formed by the semi-circular first elongate compression shaft. The first and second elongate compression shafts are, in one embodiment, constructed of a shape memory alloy such as Nitinol that may be "trained" to naturally compress to a predetermined inner diameter. In other embodiments, the compression tube may be constructed of other materials such as stainless steel, aluminum, and other various alloys and polymers that are rigid enough to maintain their overall cylindrical form, yet flexible enough to be compressed with respect to the inside diameter of the lumen of the compression tube and maintain such compression to an acceptable degree. The use of a second elongate compression shaft in conjunction with a first elongate compression shaft provides advantages in that together they provide for greater ease of compression of a surgical graft as the second elongate compression shaft can better maintain compression as compared to single shaft compression tubes. Portions (1006) of the first elongate compression tube extending outward from ends of the second elongate compression shaft provide structures which can be more easily manipulated during a surgical procedure. Further, as discussed in more detail below, such portions can be utilized to mount a removable tapered cap configured to ease the insertion of the graft-loaded compression tube into a patient. One or more first apertures (1008) are formed on the first elongate compression shaft, and one or more second apertures (1010) are formed on the second elongate compression shaft. Such first apertures and second apertures are configured to receive the hook end of tools, and in some embodiments, sutures, to assist in the removal of the compression tube from a patient after placement of a surgical graft.

Figure 11:
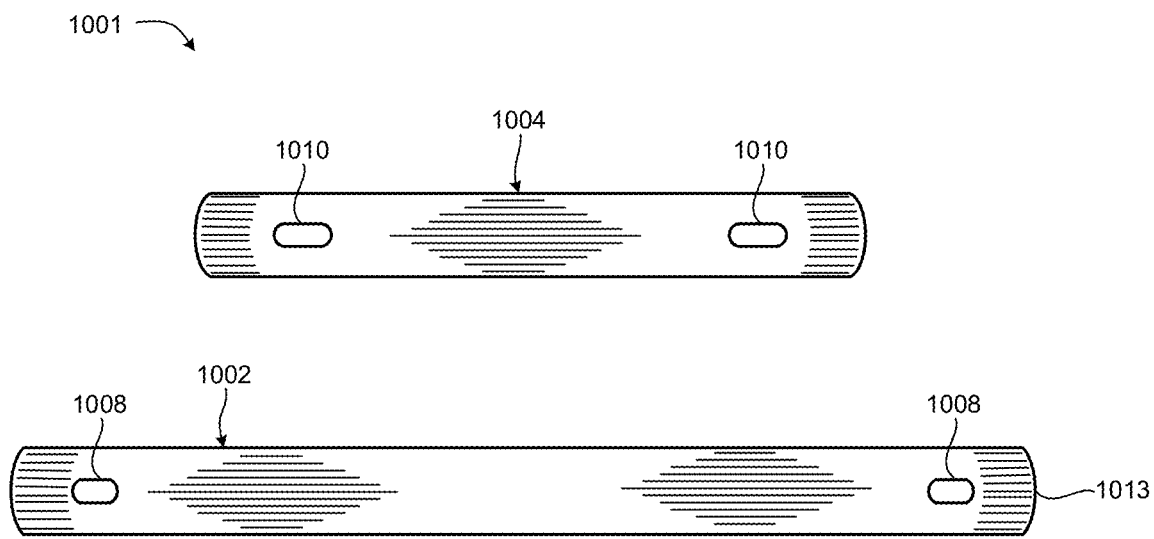
FIG. 11 is perspective view of the outer sides of the first and second elongate compression shafts of the alternate embodiment of an elongate compression tube (1001) depicted in FIG. 10.

Referring now to FIG. 11, a perspective view of the outer sides of the first and second elongate compression shafts of the alternate embodiment of an elongate compression tube (1001) depicted in FIG. 10 is shown. In one embodiment, one or both of the respective end or ends (1011, 1013) of the compression shafts may have rounded or chamfered to ease the insertion and removal of the shafts from the surgical site, reducing damage to tissue, and decreasing the forces necessary to remove the shafts.

Figure 12:
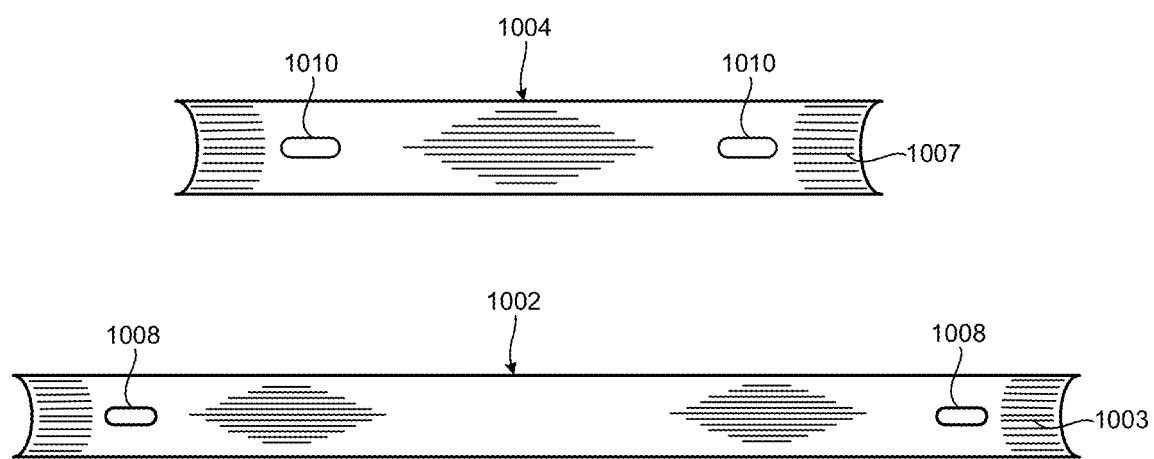
FIG. 12 is perspective view of the inner sides of the first and second elongate compression shafts of the alternate embodiment of an elongate compression tube (1001) depicted in FIG. 10.

Referring now to FIG. 12, a perspective view of the inner sides of the first and second elongate compression shafts of the alternate embodiment of an elongate compression tube (1001) depicted in FIG. 10 is shown. In one embodiment, the one or more apertures (1008, 1010) formed on the first elongate compression shaft and second elongate compression shaft, respectively, may be generally oval in shape, and sized to receive a hook shaped instrument for removal of the shafts from the surgical site. However, it is also contemplated that the apertures may be shaped and sized in alternate configurations so as to receive other types of instruments, and sutures, for the application of pulling forces on the shafts.

Figure 13:
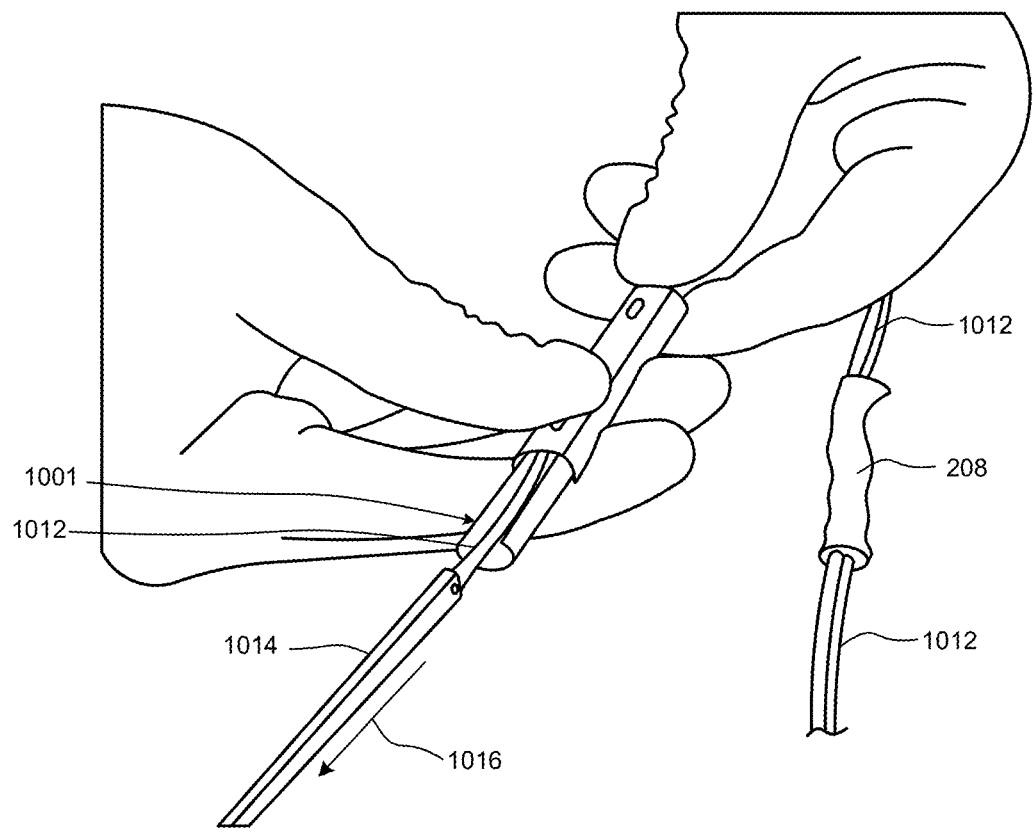
FIG. 13 is a perspective view of the alternate embodiment of the elongate compression tube depicted in FIG. 10, prepared for the loading of a surgical graft (208) for compression.

Referring now to FIG. 13, a perspective view of the alternate embodiment of the elongate compression tube depicted in FIG. 10, prepared for the loading of a surgical graft (208) for compression. A surgical graft, once appropriately sized and sutures attached to its respective ends, may be loaded/inserted into the elongate compression tube. In one embodiment, a surgeon or other medical personnel may stabilize the compression tube for loading of the graft. Alternatively, a vise or other means for securing the compression tube may be utilized to stabilize the compression tube. In one embodiment, a distal end of a grasping forceps (1014) may be inserted through the lumen of the compression tube to grasp the suture attached to the surgical graft, and then pulled back through the compression tube. Alternatively, one end of the suture (1012) attached to the graft may be fed through a lumen formed within the inner surfaces of the compression shafts. Then, a grasping forceps (1014) or other grasping/clamping instrument may be utilized to grasp the end of the suture that has been fed through the compression tube. Then, a pulling force to be applied to pull the graft through compression tube to the point that the graft is positioned within the aforementioned lumen (in other words, the portion of the compression tube where the first and second elongate compression shafts overlap).

Figure 14:
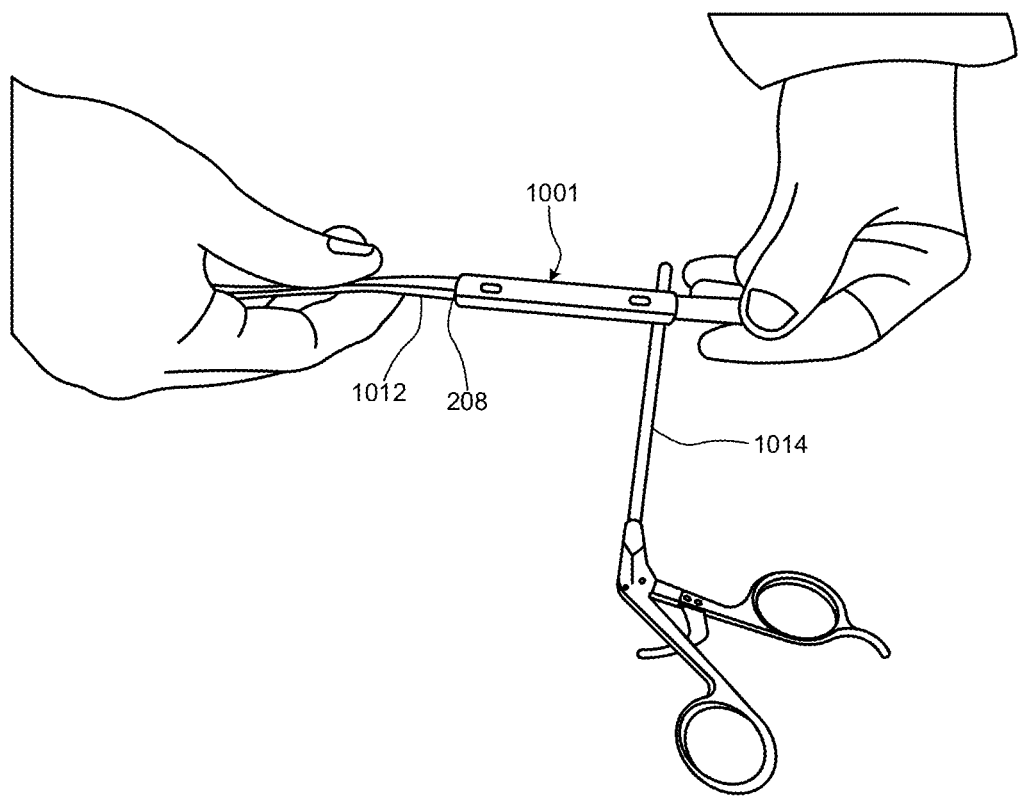
FIG. 14 is a perspective view of the alternate embodiment of the elongate compression tube depicted in FIG. 10, having a surgical graft (208) loaded within said tube for compression.

Referring now to FIG. 14, shown is a perspective view of the alternate embodiment of the elongate compression tube depicted in FIG. 10, having a surgical graft (208) loaded within said tube for compression. When the graft has been loaded/inserted into the elongate compression tube (1001), little to no portion of the graft protrudes outside of the lumen formed by the overlapping of the first and second elongate compression shafts, which helps to protect the graft during compression.

Figure 15:
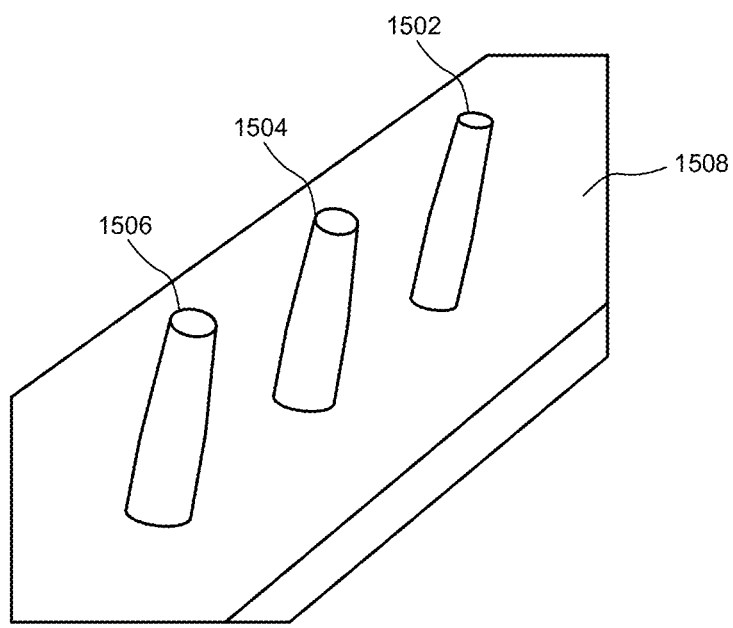
FIG. 15 are perspective views of a plurality of elongate posts configured to assist in the expansion of elongate compression tubes prior to loading/inserting a surgical graft.
Figure 15:
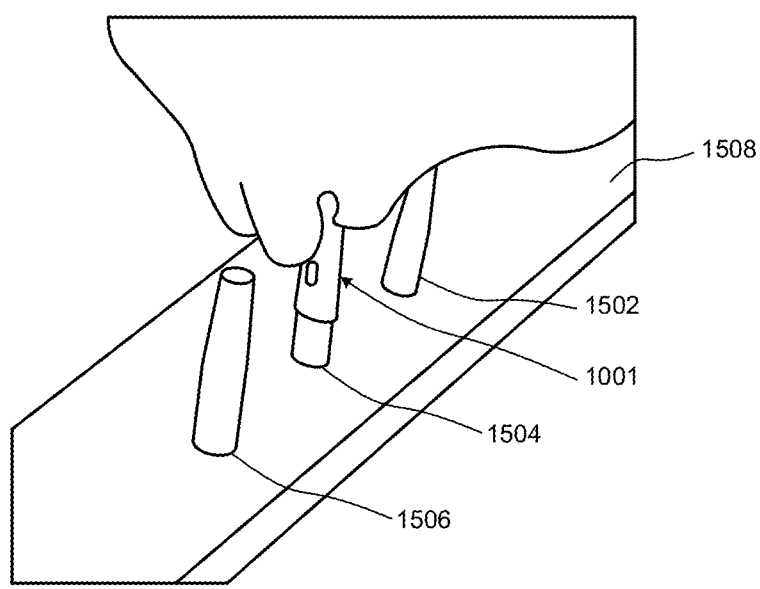

Referring now to FIG. 15, perspective views of a plurality of elongate posts configured to assist in the expansion of elongate compression tubes prior to loading/inserting a surgical graft. In one embodiment, the plurality of elongate posts (1502, 1504, 1506) each have rounded top ends, and bottom ends mounted to a base platform (1508), the base platform utilized to reduce unwanted movement as compression tubes are inserted over the posts. In one embodiment, the elongate posts are generally shaped as tapered cylinders as depicted in FIG. 15, the posts increasing in diameter from top end to bottom end such that when an elongate compression tube lumen is inserted at the top end of the post and pressed downward, the increasing diameter of the post will work to expand the diameter of the tube lumen (or in the case of expanding a compression shaft, the post will work to expand the channel). In one embodiment, the plurality of elongate posts (1502, 1504, 1506) increase sequentially in diameter at their respective bottom ends, and also at other portions of the respective posts. For example, in one embodiment, a first post (1502) may have smaller diameters along the length of the post as compared to corresponding diameters of a second post (1504). Likewise, the second post (1504) may have smaller diameters along the length of the post as compared to corresponding diameters of a third post (1506). By inserting and pressing down a compression tube from a first post, then to a second post, and then to a third post, each having progressively larger diameters, a user can gradually expand the compression tube, which can facilitate the loading of a surgical graft into the compression tube lumen before it is ultimately compressed in the graft compression system.

Figure 16:
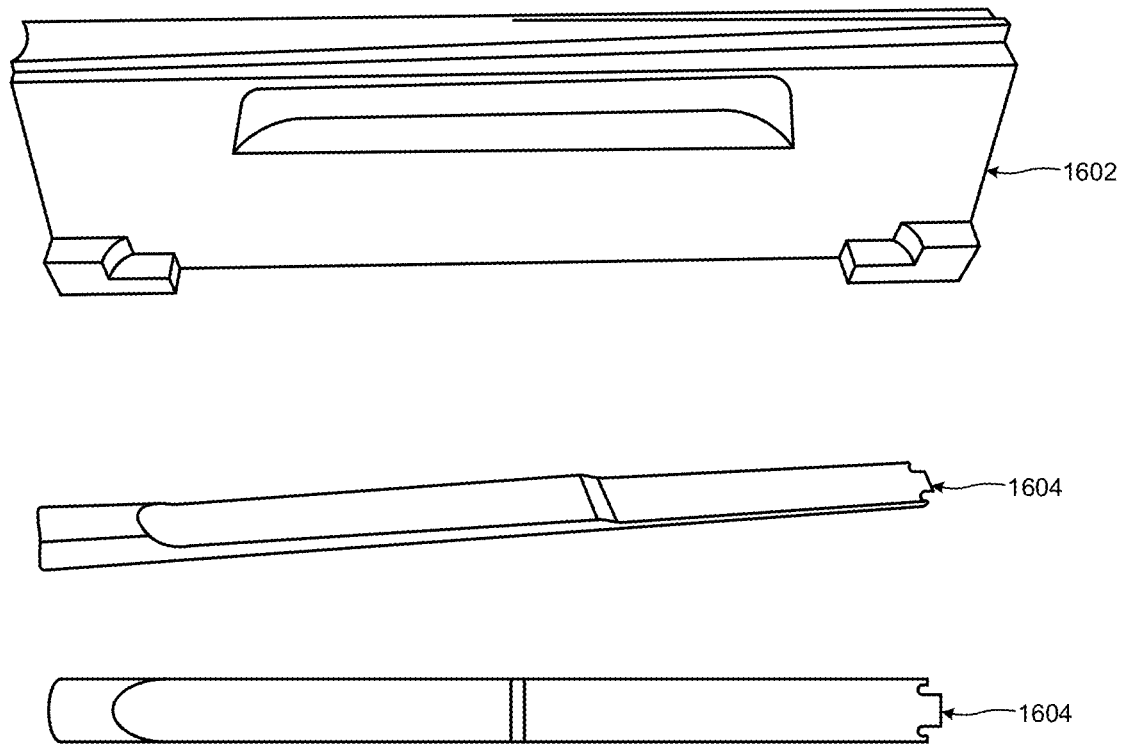
FIG. 16 are perspective views of embodiments of devices used to prepare the elongate compression tube for loading of a surgical graft.

Referring now to FIG. 16, perspective views of embodiments of devices used to prepare the elongate compression tube for loading of a surgical graft are shown. In one embodiment, a device (1602) having a tapered ridge for insertion into the gap of a compression tube such that by sliding the compression tube along such tapered ridge, the compression tube may be expanded. In one embodiment, an elongate tapered shaft (1604) may be used to facilitate such expansion of the compression tube. By using the devices to increase the diameter of the compression tube, a graft having a diameter larger than the inside diameter of the unaltered compression tube (before insertion of tool into the gap) may be inserted into such compression tube. Once a graft is inserted into the compression tube, the compressive properties of the shape memory alloy (such as Nitinol) or other material used to construct the tube, will act to compress the graft, or the graft may be further compressed by the graft compression system as described herein. Thus, the compression tube may act as a first stage of compression of the graft.

Figure 17:
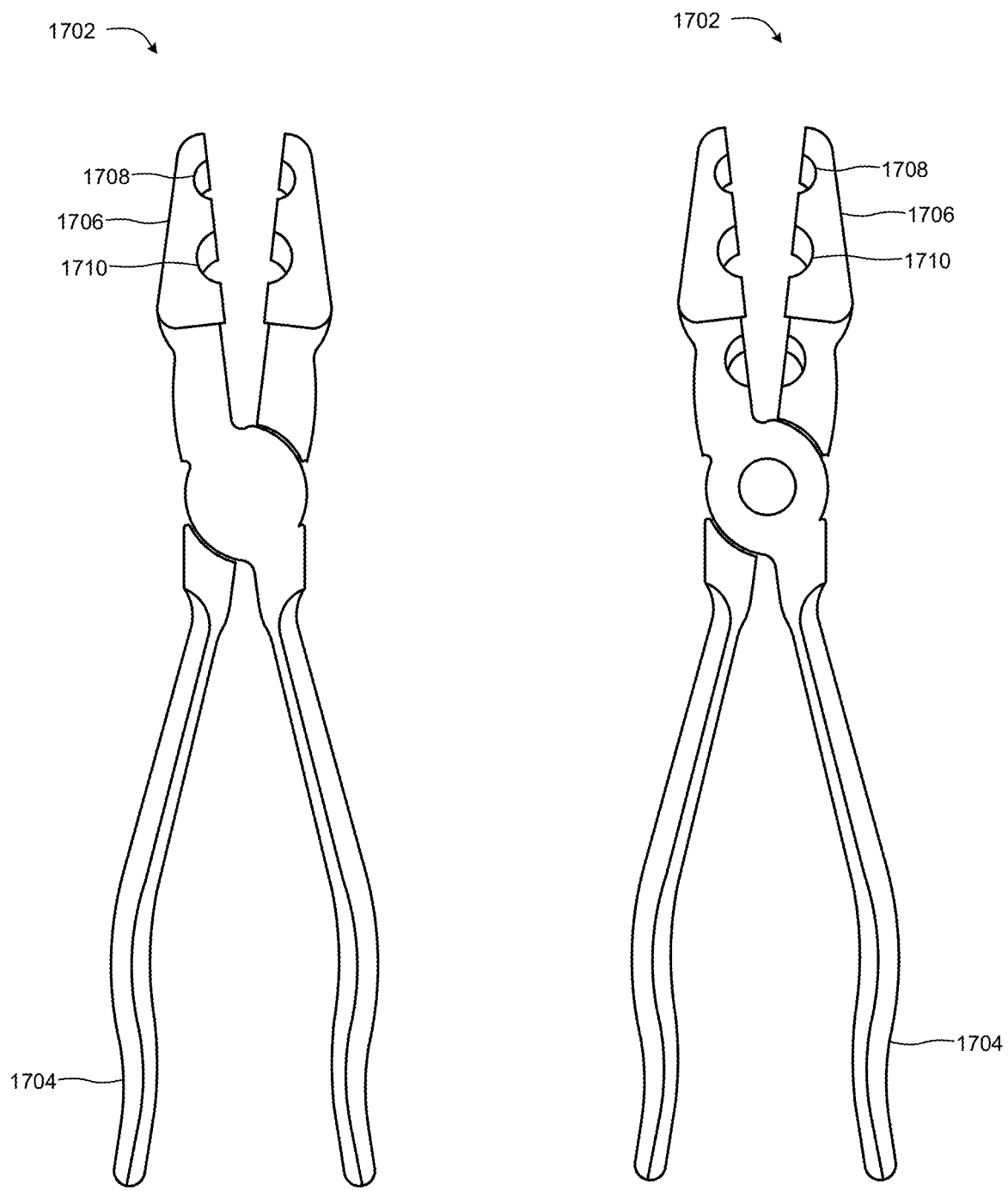
FIG. 17 is a first side view and second opposite side view of an embodiment of sequentially compressing pliers for progressively compressing an elongate compression tube loaded with a surgical graft.

Referring now to FIG. 17, a first side view and second opposite side view of an embodiment of a sequentially compressing pliers (1702) for progressively compressing an elongate compression tube loaded with a surgical graft. In one embodiment, the pliers include handles (1704) for applying a compressive force at the jaws (1706) of the pliers. The inside surfaces of the pliers jaws have semi-circular shaped indentations, said semi-circular indentations being shaped and sized to engage the outer surface of a correspondingly shaped and sized elongate compression tube loaded with a surgical graft. A plurality of semi-circular indentations area formed on the jaws of the pliers, each indentation on one jaw having a corresponding semi-circular indentation on the opposite jaw of the pliers as depicted in FIG. 17. In one embodiment, a first set of semi-circular indentations (1708) formed on opposing inside surfaces of the jaws have a smaller diameter as compared to an adjacent second set of semi-circular indentations (1710) formed on the pliers jaw. The semi-circular indentations are configured to be utilized for compressing an elongate compression tube loaded with a surgical graft. A user may utilize the pliers, applying a compressive force on the handles, to compress a compression tube inserted between a set of semi-circular indentations (1710). Then, in a sequential manner, the compression tube may be engaged by the smaller diameter set of semi-circular indentations (1708) and compressed again. In this manner, the pliers may be utilized to progressively compress the compression tube. In one embodiment, utilization of the pliers may provide a preliminary compression of the compression tube prior to further compression utilizing other compression devices described herein.

Figure 18:
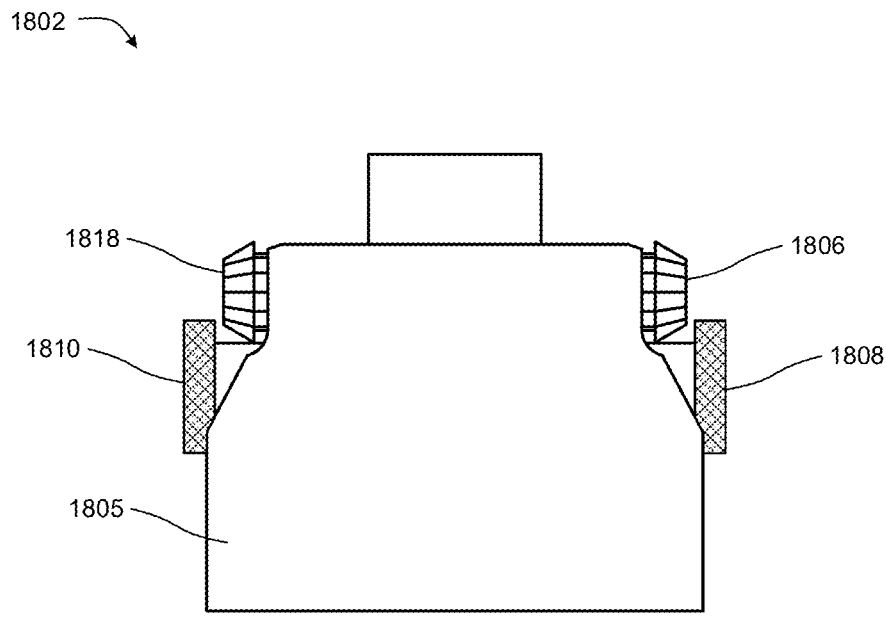
FIG. 18 is a side view of an alternate embodiment of a graft compression system.

Referring now to FIG. 18, a side view of an alternate embodiment of a graft compression system is shown. In one embodiment of the graft compression system, a compression chamber housing (1805) comprising a hollow shaft with an inner diameter greater than an outer diameter of the compression tube, is sized for the insertion of the compression tube within. A lumen within the compression chamber housing into which the compression tube may be inserted. A slot formed on a proximal collet (1806) mounted within the compression chamber housing can be engaged to reduce the diameter of the lumen formed within the collet and thereby compress an inserted compression tube and graft positioned within. Similarly, the inside lumen diameter of a distally positioned collet (1818) mounted inside the compression chamber can also be decreased via mechanical actuation as described herein, thereby further compressing the distal end of the compression tube and surgical graft within. In one embodiment, securing knobs threaded engaged to the housing on opposite side of the graft compression system housing work to secure the proximal and distal collets (1806, 1818) to the housing (1805).

Figure 19:
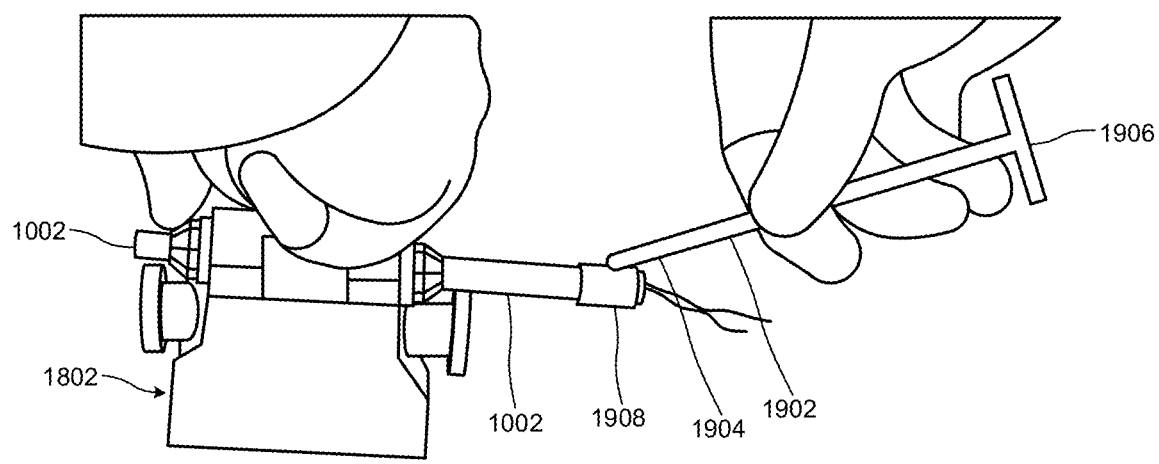
FIG. 19 is a perspective view of an embodiment of an elongate push rod (1902) having an elongate rod shaft (1904) positioned intermediate to a proximally positioned flat strike plate (1906), and a distally positioned hollow receptor (1908)

Referring now to FIG. 19, a perspective view of an embodiment of an elongate push rod (1902) having an elongate rod shaft (1904) positioned intermediate to a proximally positioned flat strike plate (1906), and a distally positioned hollow receptor (1908). In one embodiment, the distally positioned hollow receptor (1902) has a lumen sized to receive and temporarily mate with an end of a first elongate compression shaft (1002). The hollow receptor (1908), having a generally cylindrical shape, is configured to slide onto the end of the first elongate compression shaft such that a pushing force applied at the strike plate (1906) is transferred through the shaft (1904) and applied at the first elongate compression shaft to assist in pushing the compression tube into the graft compression system (1802). In one embodiment, a mallet may be used to strike the strike plate, thereby pushing the compression tube into the graft compression system. In one embodiment, the connection between the shaft (1904) and receptor (1908) is fixed. In other embodiments, the shaft (1904) and receptor (1908) are pivotally attached (for example, ball and socket joint). An advantage of utilizing the elongate push rod is that a pushing force can be applied to insert the compression tube into the graft compression system without damaging the sutures, the compression tube, or the surgical graft.

Figure 20:
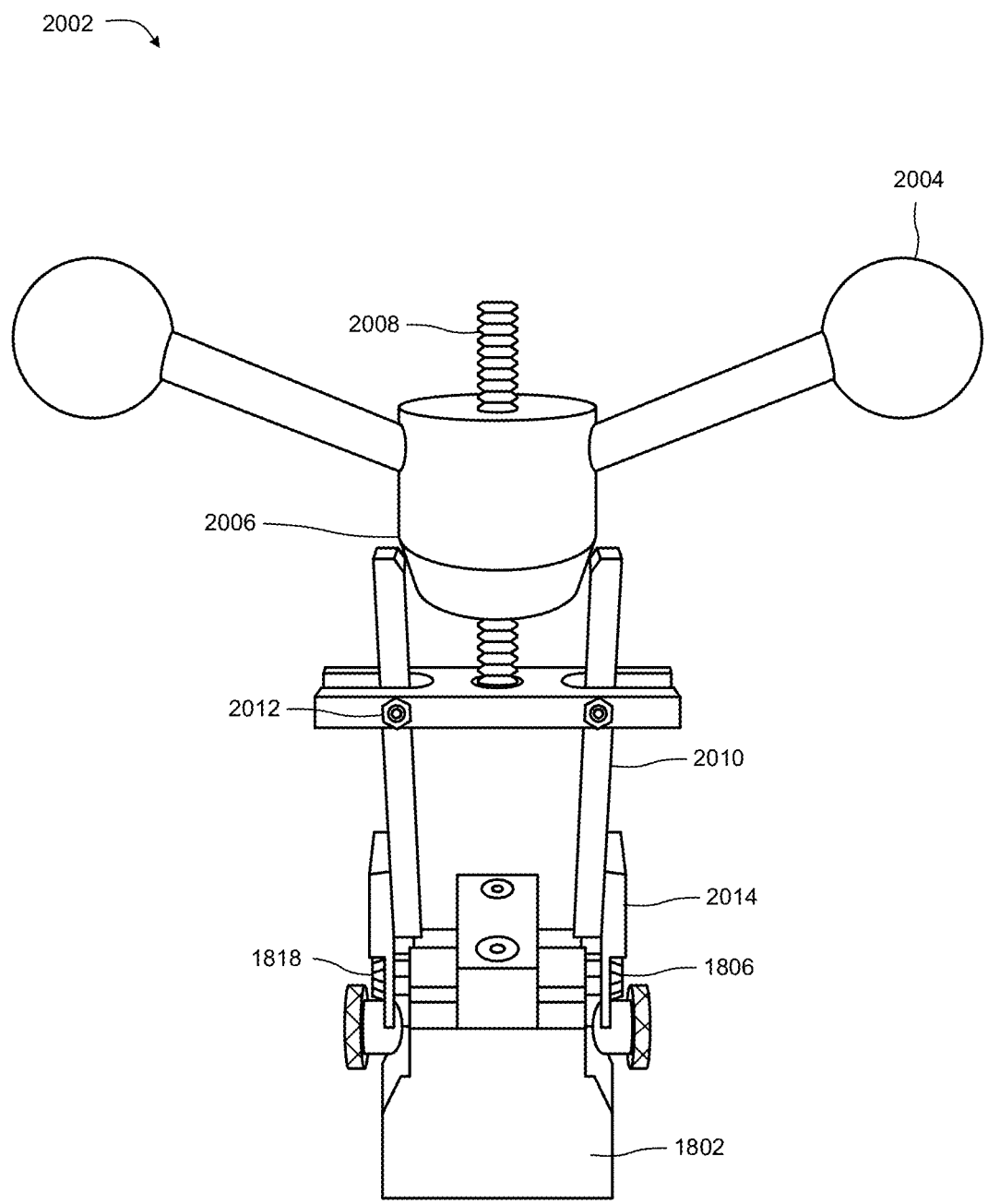
FIG. 20 is a perspective view of an embodiment of an improved collet wrench connected to the alternate embodiment of the graft compression system depicted in FIG. 18.

Referring now to FIG. 20, shown is a perspective view of an embodiment of an improved collet wrench connected to the collet slots of collets in the alternate embodiment of the graft compression system depicted in FIG. 18. In one embodiment, an improved collet wrench (2002) has an upper end having one or more handles (2004) attached to a substantially cylindrical wrench barrel (2006) having a threaded hollow aperture through which a correspondingly threaded through bolt (2008) passes such that a user may use the handles (2004) to rotate the wrench barrel (2006) up and down the through bolt (2008). In one embodiment, a tapered lower end of the wrench barrel (2006) is positioned to press, when traveling downward, against upper ends of wrench control arms (2010). As the upper portion of the control arms are gradually pushed outward by the tapered wrench barrel, pins attached on the shafts of the control arms cause the lower portion of the control arms to move inward. Attached to the lower end of each control arms is a collar (2014) configured to engage each respective slot on the proximal (1806) and distal (1818) collets of the graft compression system, such that inward movement of the collars (attached to lower ends of control arms) works to compress the inner diameters of the collets, thereby compressing an elongate compression tube inserted into the graft compression system.

Referring now to FIG. 21A, shown is perspective view of a bullet-shaped hollow insertion cap (2102), as depicted in FIG. 21B and FIG. 21C, mounted on a proximal end of the embodiment of the elongate compression tube (with compressed surgical graft within) as depicted in FIG. 14, ready for insertion into an incision in a patient. The hollow insertion cap facilitates insertion of the elongate compression tube into the incision, and delivery of the tube and compressed surgical graft. Referring now to FIG. 21B and FIG. 21C, shown are first and second opposing side views of the hollow insertion cap (2102) for mounting on a proximal end of an embodiment of the elongate compression tube (with compressed surgical graft within) as depicted in FIG. 21A. In one embodiment of the hollow insertion cap (2102), a distal portion of the cap body is rounded or blunted to facilitate passage of the compression tube into the patient and to the location within the patient where the graft will be delivered. A length of the proximal portion of the cap body is substantially cylindrical in shape, such length of the proximal portion being adjacent to a distal portion of the cap body that has a continuously decreasing thickness terminating at the rounded or blunted distal end of the cap body. The substantially cylindrical shape of the proximal portion of the cap body is shown in FIG. 21A, depicting a proximal end of the elongate compression tube inserted into the circular shaped proximal open end of the cap body of the insertion cap. In one embodiment, the cap (2102) includes a proximally positioned round opening at a proximal end (2106), said opening sized and shaped to removably mate with a distal end of an elongate compression shaft (1002) of a compression tube (1001). In one embodiment, the cap is cannulated (2108) at its distal end (2104) to allow for passage of suture line used to pull the compression tube (with graft) to the surgical site. In one embodiment, the cap has a channel (2112) formed along a length of at least one side of the proximal portion of cap body and distal portion of the cap body, allowing suture line to pass unimpeded in such channel. A distal end of such channel is positioned at a cannulated opening on the distal end of the distal portion of the cap body. A proximal end of such channel is positioned at the proximally positioned round opening. In one embodiment, a slot (2110), hole, or aperture is formed on one or more sides of the cap, said slot, hole, or aperture is shaped and sized to be engaged by a hook or other instrument structure (see FIG. 22) utilized to remove the cap once the graft has successfully been positioned at the surgical site. In one embodiment, the slot or aperture (2110) runs completely through the cap, from one side to the other side. In alternate embodiment, the slot or aperture (2110) does not run completely through the cap. In one embodiment, the slot, hole, or aperture (2110) is oval or oblong shaped, and positioned within the aforesaid channel at least on one side of the cap body. In one embodiment, a portion of the slot or aperture is positioned on part of the distal portion of the cap body, and another portion of the slot or aperture is positioned on part of the proximal portion of the cap body. In other alternate embodiments, the slot or aperture is positioned on one of the distal portion of the cap body or proximal portion of the cap body.

Figure 22:
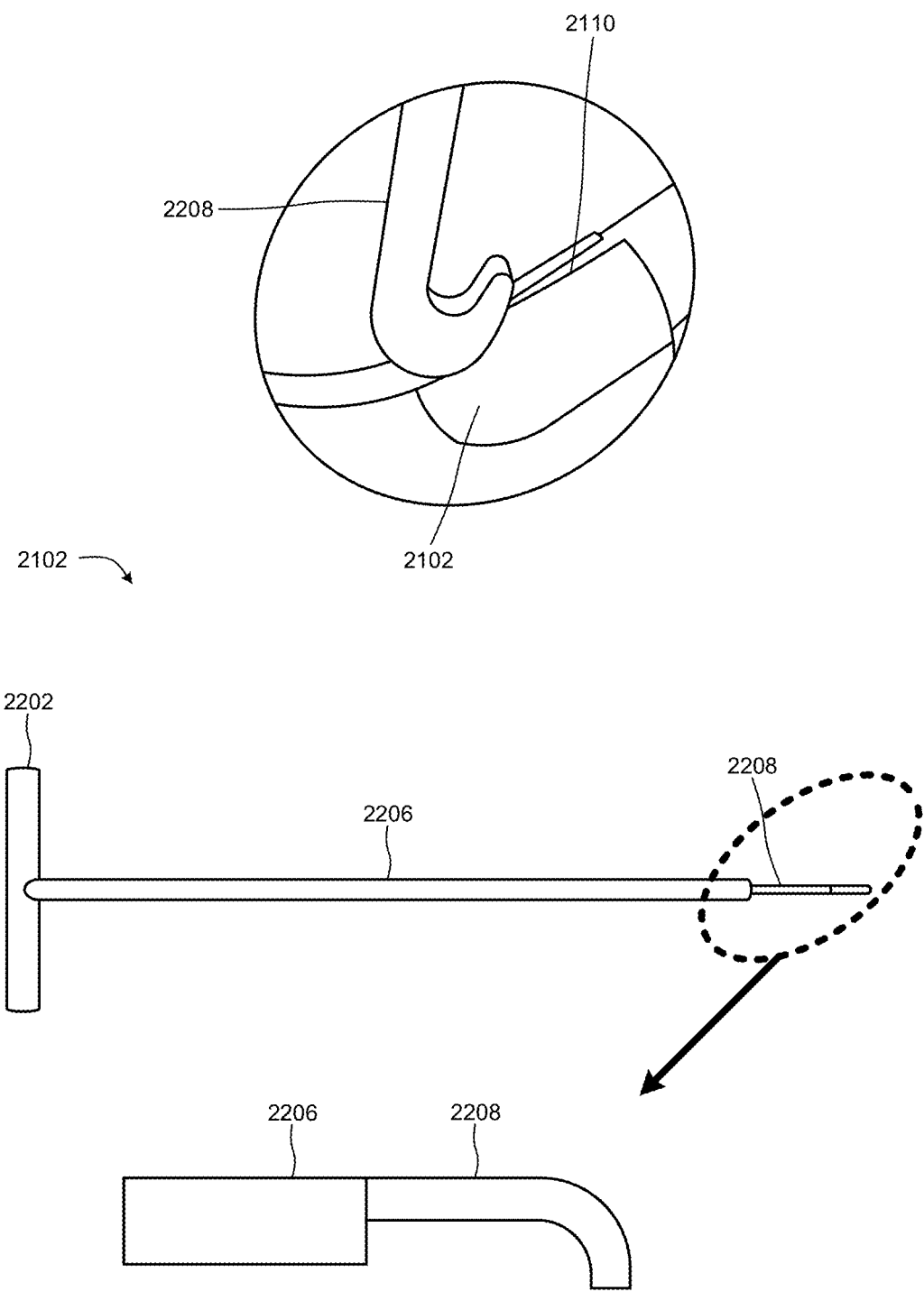
FIG. 22 are perspective views of an embodiment of an elongate hook device configured to remove embodiments of the insertion cap and compression tube following delivery of the graft to the surgical site.

Referring now to FIG. 22, shown are perspective views of an embodiment of an elongate hook device (2202) configured to remove embodiments of the insertion cap (2102) and compression tube following delivery of the graft to the surgical site. In one embodiment, the elongate hook device includes a "T" handle (2204) fastened or fixed onto a proximal end and connected to an elongate shaft (2206) having a length that will permit a distal mounted hook end (2208) to reach a surgical site. In one embodiment, the hook end (2208) is shaped and sized to engage a correspondingly shaped and sized slot (2110) of an insertion cap (2102). Using the elongate hook device, or another instrument having a hook, a surgeon can insert the device/instrument into the incision and engage the slot (2110) of the insertion cap (mounted to end of compression tube) at the surgical site to remove the cap from the compression tube and pull it from the patient. Likewise, using the elongate hook device, or another instrument having a hook, a surgeon can insert the device/instrument into the incision and engage the apertures (1008, 1010) of the compression shafts to remove them from the patient upon successful delivery of the surgical graft.

Figure 23:
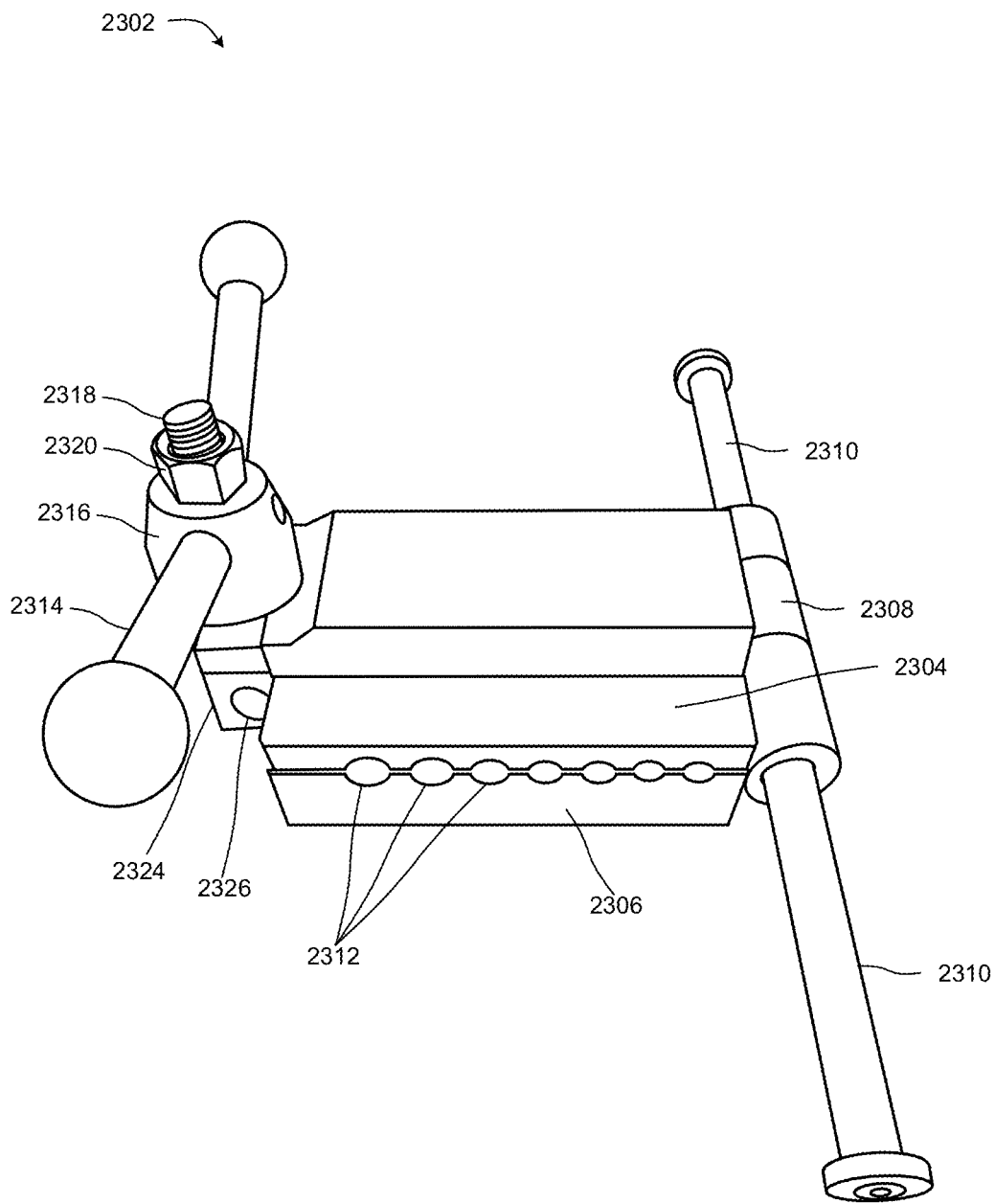
FIG. 23 is a perspective view of an alternate embodiment of a graft compression system in a closed configuration.

Referring now to FIG. 23, shown is a perspective view of an alternate embodiment of a graft compression system (2302) in a closed configuration. In this alternate embodiment, the graft compression system (2302) includes a top/upper press body (2304) coupled to a bottom/lower press body (2306) via a hinge (2308). In one embodiment, a single hinge knuckle is formed on an end of the top press body (2304), and two hinge knuckles are formed on the end of the bottom press body (2306) such that the top press body and bottom press body act as hinge plates. A substantially cylindrical elongate shaft (2310) is inserted through the holes in the respective hinge knuckles, which serve as a hinge pin around which the top press body and bottom press body may pivot so as to open and close the graft compression system. The elongate shaft that serves as a hinge pin has opposing ends that extend well beyond the ends of the respective opposing hinge knuckles from which they protrude. Exposed sections of the elongate shaft (2310) preferably have lengths that are sufficient for a user to grasp with hands so as to stabilize the graft compression system when in use. In one embodiment, the elongate shaft/pivot pin has opposing ends each having lengths that protrude beyond the respective lateral sides of said top/upper press body and said bottom/lower press body. The exposed sections of the elongate shaft may be held by a user in a static position so as to resist rotational and other forces on the graft compression system as screw press handle (2314) is rotated by a second user in order to compress the top press body and bottom press body. In some embodiments, the pivot pin/elongate shaft is the same structure that may be grasped by a user to stabilize the graft compression system. In other embodiment, one structure may serve as a pivot pin to couple the top/upper press body and bottom/lower press body, while one or more other structures attached to said graft compression system may serve as stabilizing handles or shafts. While the elongate shaft (2310) depicted as perpendicular, alternate embodiments of the graft compression system may feature shafts and shaft segments with combinations of perpendicular and vertical (and angled) shafts/shaft segments having various shapes and diameters that facilitate a user grasping the shaft/shaft segments to hold the graft compression system in place during the compression process. In one embodiment, ends of the elongate shafts may be contoured to provide gripping surfaces. In other alternate embodiments, the elongate shaft (2310) may be absent, and the graft compression system may be fastened, attached, mounted, or formed on a static surface such that it is not necessary for a user to hold it in place during the compression process. It should be noted that the term "screw press" is utilized herein to describe aspects of embodiments of the graft compression system on the basis that some of the components of such embodiments are similar to some components of a screw press. However, it should be recognized that not all aspects of the embodiments of the graft compression system associated with such term are necessarily the same structure as, or operate the same as, the components of a traditional screw press found in the prior art.

Still referring to FIG. 23, the respective interior surfaces of the top press body and bottom press body abut one another in a closed configuration as depicted such that a plurality of semi-circular channels formed on said interior surfaces are in substantial alignment with one another to form one or more cylindrical compression apertures (2312). The plurality of cylindrical compression apertures (2312) each have diameters that decrease sequentially from one end of the graft compression system to the other (conversely, the diameters of the compression apertures likewise increase sequentially from the opposing end of the graft compression system to the other). While the compression apertures depicted in connection with the embodiment of the graft compression system depicted in FIG. 23 decrease sequentially from the end adjacent to the screw press handle (2314), to the end adjacent to the elongate shaft (2310), alternate embodiments of the graft compression system may instead feature compression apertures that decrease in diameter in the opposite direction. Each of the plurality of cylindrical compression apertures is sized and shaped to receive an elongate compression tube loaded with a surgical compression graft. By sequentially placing an elongate compression tube in one or more of the plurality of compression apertures, and compressing them in a sequential manner as described herein, the graft compression system may be utilized to sequentially compress an elongate compression tube in stages so that its diameter is sequentially decreased, which will in turn decrease the diameter of the surgical graft loaded within such elongate compression tube.

Still referring to FIG. 23, the graft compression system includes a screw press barrel (2316) and screw press handles (2314) formed on such screw press barrel and extending outward and angled upwardly. The screw press barrel (2316) is threadedly attached to an upper portion of a threaded eye bolt shaft (2318), the lower portion of said eye bolt shaft having an eyelet (see FIG. 24 at 2322) formed thereon and is pivotally coupled to the bottom press body via a pin (2326) that is inserted through the eyelet, said pin having opposing sides attached to a lower U-shaped clevis or "knuckle" structure (2324) protruding outwardly in a lateral direction from the end of the bottom press body. The eye bolt shaft and U-shaped clevis/knuckle structure are attached to one another in a "knuckle joint" or "hinge joint" type coupling that allows for rotational movement about the pin that passes through the eyelet of the eye bolt. A nut (2320) is threaded onto the upper end of the eye bolt shaft and works to secure the screw barrel (2316) to the eye bolt shaft (2318). In one embodiment, the nut is attached to the screw barrel, but in other embodiments, the nut is not attached to the screw barrel, and works to limit the uppermost travel of the screw barrel on the eye bolt shaft. When the graft compression system is in a closed configuration, a user may rotate the screw barrel by grasping the screw press handles and applying a twisting/rotating motion so as to cause the screw barrel to travel in a downward direction along the eye bolt shaft (the direction in which the handles must be rotated to tighten or loosen the compression of the graft compression system will depend on whether the threading of the eye bolt is left-hand or right-hand). The bottom of the screw barrel, when the graft compression is in a closed configuration, will abut the top of the top press body and top side of an upper U-shaped clevis/knuckle structure (2330) formed on the end of said top press body such that as the screw press barrel continues to travel downward along the eye bolt shaft due to the twisting motion imparted on the screw press handles by a user, the top press body and bottom press body will compress together. As the top press body and bottom press body compress together, any elongate compression tube loaded with a surgical graft that has been inserted into a compression aperture (2312) will likewise be compressed.

Figure 24:
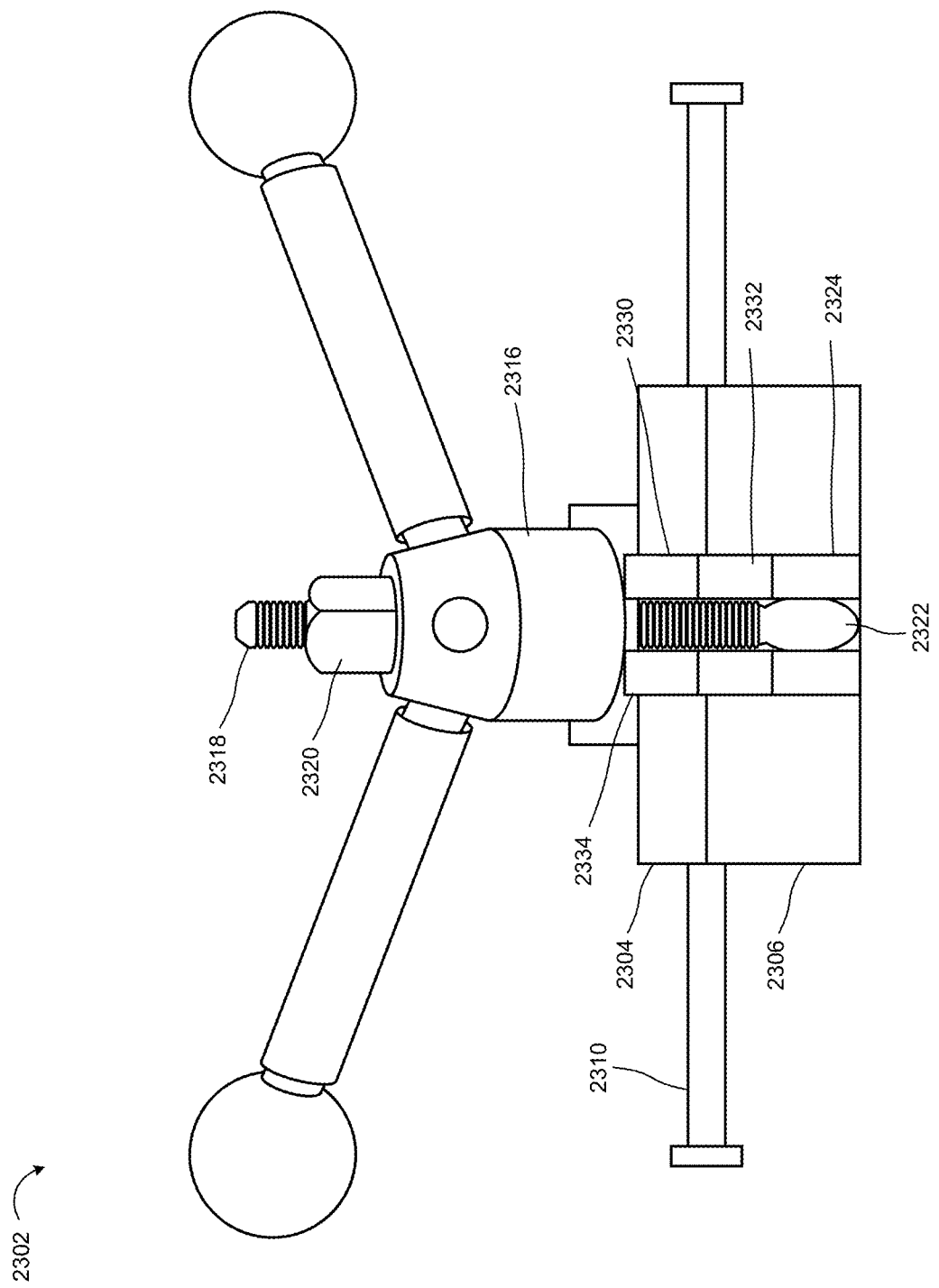
FIG. 24 is a front view of the alternate embodiment of a graft compression system in a closed configuration as depicted in FIG. 23.

Referring now to FIG. 24, shown is a front view of the exterior of the alternate embodiment of a graft compression system in a closed configuration as depicted in FIG. 23. As described above, the screw press barrel (2316) is threadedly attached to an upper portion of a threaded eye bolt shaft (2318), the lower portion of said eye bolt shaft having an eyelet (2322) formed thereon and is pivotally attached to the bottom press body via a pin (see FIG. 23 at 2326) that is inserted through the eyelet, said pin positioned within holes formed in the lower U-shaped clevis or "knuckle" structure (2324) protruding outwardly in a lateral direction from the end of the bottom press body (2306). The eyelet (2322) of the eye bolt shaft (2318) and lower U-shaped clevis/knuckle structure (2324) are attached to one another in a "knuckle joint" or "hinge joint" type coupling utilizing a pin (see FIG. 23 at 2326) that allows for rotational movement about the pin that passes through the eyelet of the eye bolt. A first upper U-shaped clevis/knuckle structure (2330) protrudes outwardly in a lateral direction from the end of the top press body (2304), the eye bolt shaft (2318) being configured to pass through such structure. In one embodiment, as depicted in FIG. 24, a second upper U-shaped clevis/knuckle structure (2332), positioned below the first upper U-shaped clevis/knuckle structure (2330), protrudes outwardly in a lateral direction from the end of the top press body (2304), the eye bolt shaft (2318) being configured to pass through such structure. When the graft compression system (2302) is in a closed configuration, a user may rotate the screw barrel (2316) by grasping the screw press handles (2314) and applying a twisting/rotating motion so as to cause the screw barrel to travel in a downward direction along the eye bolt shaft (2318) (the direction in which the handles must be rotated to tighten or loosen the compression of the graft compression system will depend on whether the threading of the eye bolt is left-hand or right-hand). The bottom of the screw barrel, when the graft compression is in a closed configuration, will abut the top of the top press body (2304) and top side (2334) of the upper U-shaped clevis/knuckle structure (2330) formed on the end of said top press body such that as the screw press barrel continues to travel downward along the eye bolt shaft due to the twisting/rotating motion imparted on the screw press handles by a user, the top press body and bottom press body will compress together. As the top press body and bottom press body compress together, any elongate compression tube loaded with a surgical graft that have been inserted into one of the compression apertures (2312) will likewise be compressed.

Figure 25:
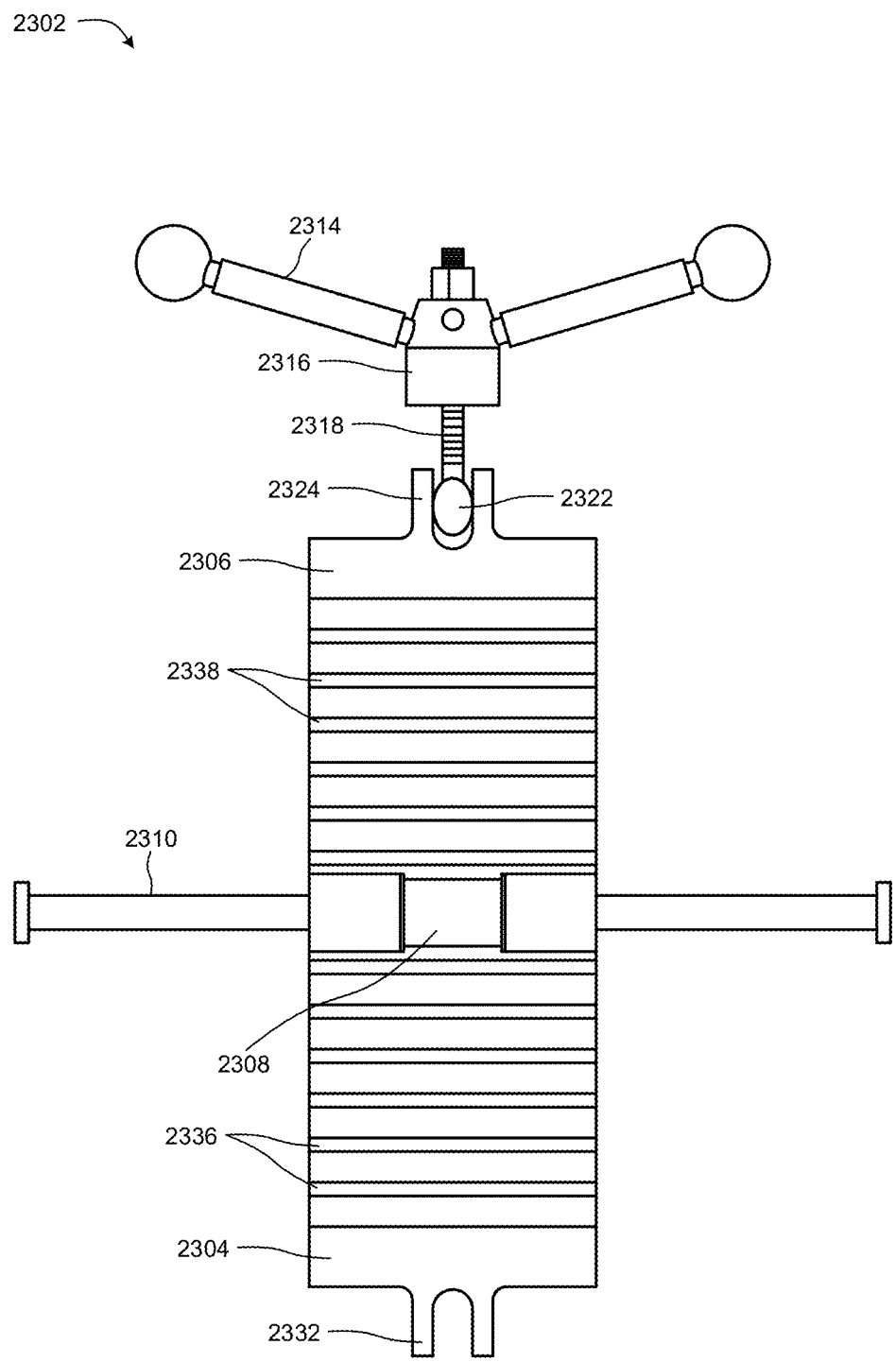
FIG. 25 is a perspective view of the alternate embodiment of a graft compression system as depicted in FIG. 23, now shown in a fully open configuration.

Referring now to FIG. 25, a perspective view of the alternate embodiment of a graft compression system as depicted in FIG. 23, now shown in a fully open configuration. In this fully open configuration, the screw press barrel (2316) is not engaged with either of the first or second upper U-shaped clevis/knuckle structures (2330, 2332) formed on the end of the top press body (2304). The hinges (2308) of the graft compression system are configured, in one embodiment, to allow the top press body (2304) and bottom press body (2306) to lay flat on their respective exterior sides as depicted in FIG. 25. A plurality of top semi-circular channels (2336) are formed on the interior surface of the top press body (2304). A plurality of bottom semi-circular channels (2338) are formed on the interior surface of the bottom press body (2306). When the graft compression system is place in a closed configuration (when the top and bottom press bodies are rotated about the hinge to abut on another as depicted in FIG. 23), the plurality of top semi-circular channels (2336) and the plurality of bottom semi-circular channels (2338) become aligned to form the plurality of compression apertures.

Still referring to FIG. 25, when the graft compression system is positioned in an open configuration, an elongate compression tube may be placed in one of the bottom semi-circular channels (2338). Next, the top press body may be rotated about the hinge (2308) until the graft compression system is positioned in a closed configuration as depicted in FIG. 23. Next, a user should confirm that the elongate compression tube is properly seated in a compression aperture formed by a top semi-circular channel aligned with a bottom semi-circular channel. When an elongate compression tube is inserted into the compression aperture, the tops of the opposing semi-circular channels will not abut one another, at least until a user compresses the top press body and bottom press body together (the tops of the opposing semi-circular channels depicted in FIG. 23 are shown to abut one another, there being no elongate compression tubes inserted into the compression apertures). Next, a user will rotate the screw press barrel on the top side of the upper U-shaped clevis knuckle structure, about the pin inserted through the eyelet (it may be necessary to first rotate the screw barrel to cause it to travel along the eye bolt shaft sufficiently away from the eye bolt eyelet to allow the screw barrel to be positioned on top of the upper U-shaped clevis knuckle structure). Next a user will utilize the handles (2314) to rotate/twist the screw barrel such that it travels towards the eyelet of the threaded eye bolt shaft, thereby compressing the top press body into the bottom press body, and as a result compressing the top and bottom semi-circular channels to compress the inserted elongate compression tube (with loaded surgical graft). Preferably a second user will grasp the elongate shafts (2310) to keep the graft compression system from moving as torque is applied by the first user on the screw press handles. Once the elongate compression tube has experience one stage of compression, the screw press handles may be rotated so as to take the top press body and bottom press body out of compression, and allow the graft compression system to be placed once again in an open configuration. Next, the elongate compression tube may be removed from the original semi-circular channel in which it was placed, and further placed in a new semi-circular channel having a decreased channel diameter. Next, the graft compression system may be placed again in a closed configuration and the system compressed once again. This process may be repeated on or more times, each time placing the elongate compression tube in a semi-circular channel/compression aperture having a smaller diameter. By sequentially placing an elongate compression tube in the one or more of the plurality of compression apertures having ever smaller diameters, and compressing them in a sequential manner as described herein, the graft compression system may be utilized to sequentially compress an elongate compression tube so that its diameter is sequentially decreased so as to decrease the diameter of the surgical graft loaded within such elongate compression tube.

Figure 26:
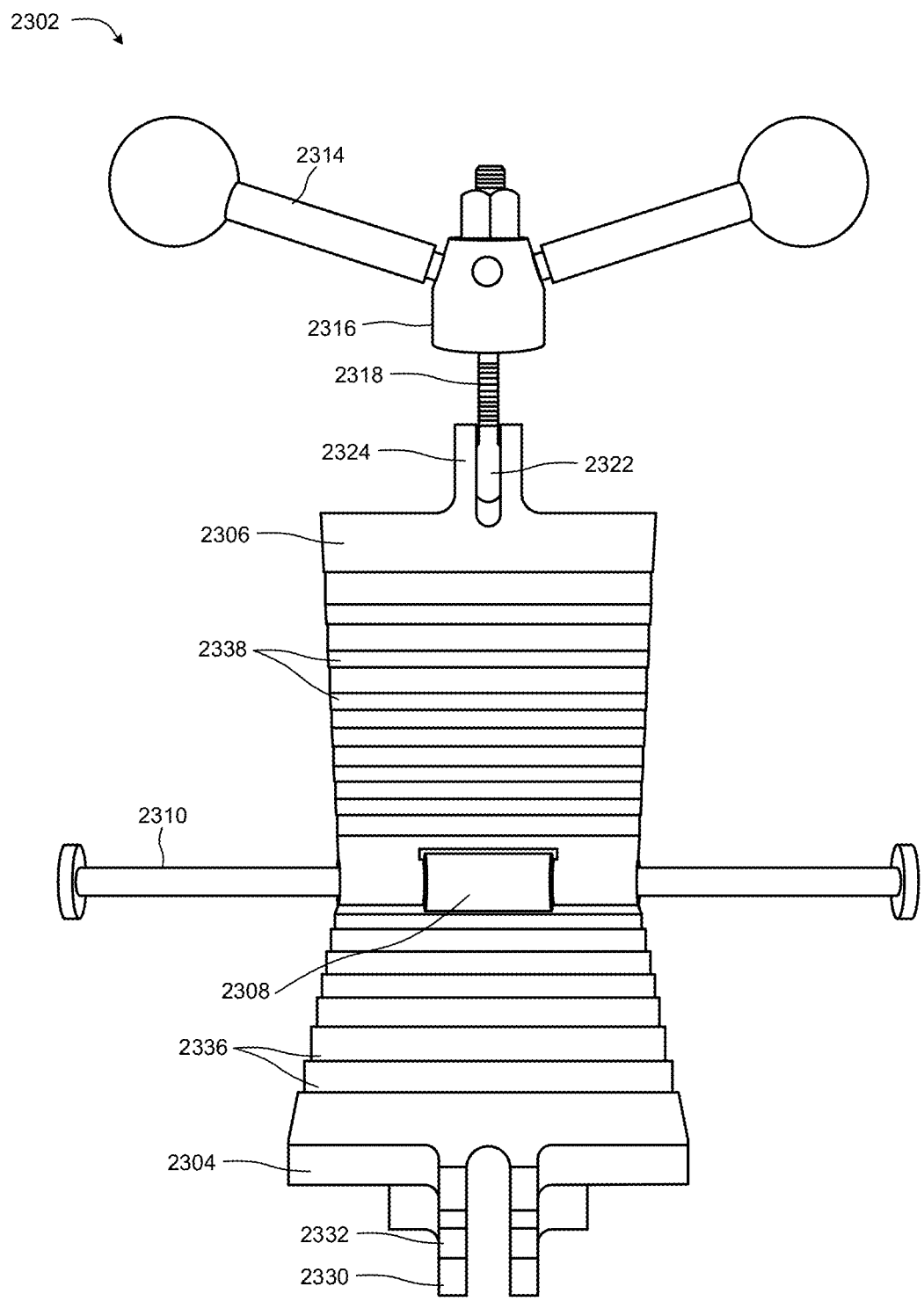
FIG. 26 is a perspective view of the alternate embodiment of a graft compression system as depicted in FIG. 23, now shown in a partially open configuration.

Referring now to FIG. 26, a perspective view of the alternate embodiment of a graft compression system as depicted in FIG. 23, now shown in a partially open configuration. In this partially open configuration, the screw press barrel (2316) is not engaged with either of the first or second upper U-shaped clevis/knuckle structures (2330, 2332) formed on the end of the top press body (2304). The hinges (2308) of the graft compression system are configured, in one embodiment, to allow the top press body (2304) and bottom press body (2306) to be positioned at an approximately ninety-degree angle to one another as depicted in FIG. 26. A first upper U-shaped clevis/knuckle structure (2330) protrudes outwardly in a lateral direction from the end of the top press body (2304), the eye bolt shaft (2318) being configured to pass through such structure when the graft compression system is placed in a closed configuration for compression. In one embodiment, as depicted in FIG. 26, a second upper U-shaped clevis/knuckle structure (2332), positioned below the first upper U-shaped clevis/knuckle structure (2330), protrudes outwardly in a lateral direction from the end of the top press body (2304), the eye bolt shaft (2318) being configured to pass through such structure when the graft compression system is placed in a closed configuration for compression. It should be noted that while the alternate embodiments of the graft compression system depicted in FIGS. 23-26 are constructed of metal (for example, stainless steel), even further alternate embodiments may be constructed of other materials that have properties sufficient to perform the compression stages described herein. Ideally, such materials will be capable of being utilized in a surgical environment. In one embodiment, a surgical graft compression system (2302) is disclosed, said surgical graft compression system including an upper press body (2304) having a first end and opposing second end, said upper press body having a first inner side having a first plurality of parallel semi-circular shaped channels formed thereon; and a lower press body having a third end and opposing fourth end, said lower press body having a second inner side having a second plurality of parallel semi-circular shaped channels formed thereon, wherein said upper press body is pivotally coupled to said lower press body at said first end and said third end, respectively, wherein each of said first plurality of parallel semi-circular shaped channels are formed to have sequentially decreasing channel widths, wherein each of said second plurality of parallel semi-circular shaped channels are formed to have sequentially decreasing channel widths, wherein said upper press body and said lower press body are configured to pivot about a pivot pin such that said first inner side of said upper press body abuts said second inner side of said lower press body such that said first plurality of parallel semi-circular shaped channels are substantially aligned with said a said plurality of parallel semi-circular shaped channels. In one embodiment, a screw press barrel is attached to an upper portion of a threaded eye bolt shaft, a lower portion of the eye bolt shaft having an eyelet formed thereon and is pivotally coupled to the fourth end of said lower press body via a pin. In another embodiment, the graft compression system has one or more outwardly projecting handles are attached to said screw press barrel. In another embodiment, a bottom end of the screw press barrel is configured to abut an outer side of said upper press body to compress said upper press body with said lower press body. In one embodiment, the eye bolt shaft has a threaded exterior along at least a portion of the shaft length. The screw press barrel has a correspondingly threaded hole formed within in it, running from the top end of the barrel to the bottom end of the barrel. The eye bolt shaft is configured to threadedly engage the threaded hole of the screw press barrel, and the screw press barrel is configured to travel along the shaft of the eye bolt. The outwardly projecting handles on the screw press barrel allow a user to rotate the screw press barrel to cause the barrel to travel along the eye bolt shaft.

Figure 27:
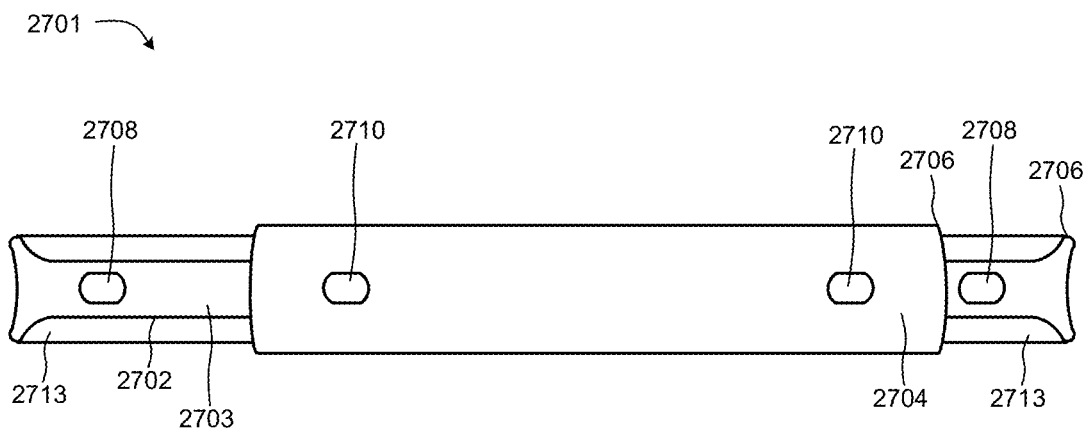
FIG. 27 is a perspective view of a further alternate embodiment of an elongate compression tube.

Referring now to FIG. 27, a perspective view of a further alternate embodiment of an elongate compression tube (2701) is shown. The embodiment of the elongate compression tube depicted in FIG. 27 is an many respects identical to the elongate compression tube depicted in FIGS. 10-13. One notable difference is that the alternate embodiment of the elongate compression tube in FIG. 27 is that it includes a first elongate compression shaft (2702) having chamfered/sloped ends (2713) to facilitate the insertion of the elongate compression tube into an incision site, and to reduce tissue damage as the tube travels to and from the surgical site. Like the embodiment of the elongate compression tube depicted in FIGS. 10-13, the alternate embodiment of an elongate compression tube (2701) includes a first elongate compression shaft (2702) configured to mate with a second elongate compression shaft (2704). In one embodiment, the first elongate compression shaft (2702) has a longer length than the second elongate compression shaft (2704). In one embodiment, the second elongate compression shaft (2704) is configured to have a length substantially equal to a length of a graft prepared to be loaded into the elongate compression tube for compression. As seen in FIG. 27, the second elongate compression shaft has a slightly larger cross-sectional diameter as compared to the first elongate compression shaft, allowing the second elongate compression shaft to mounted on top of the channel (2703) formed by the semi-circular first elongate compression shaft. The first and second elongate compression shafts are, in one embodiment, constructed of a shape memory alloy such as Nitinol that may be "trained" to naturally compress to a predetermined inner diameter. In other embodiments, the compression tube may be constructed of other materials such as stainless steel, aluminum, and other various alloys and polymers that are rigid enough to maintain their overall cylindrical form, yet flexible enough to be compressed with respect to the inside diameter of the lumen of the compression tube and maintain such compression to an acceptable degree. The use of a second elongate compression shaft in conjunction with a first elongate compression shaft provides advantages in that together they provide for greater ease of compression of a surgical graft as the second elongate compression shaft can better maintain compression as compared to single shaft compression tubes. Portions (2706) of the first elongate compression tube extending outward from ends of the second elongate compression shaft provide structures which can be more easily manipulated during a surgical procedure. Further, as has been previously discussed in more detail above, such portions can be utilized to mount a removable tapered cap configured to ease the insertion of the graft-loaded compression tube into a patient. One or more first apertures (2708) are formed on the first elongate compression shaft, and one or more second apertures (2710) are formed on the second elongate compression shaft. Such first apertures and second apertures are configured to receive the hook end of tools, and in some embodiments, sutures, to assist in the removal of the compression tube from a patient after placement of a surgical graft. In one embodiment, the one or more apertures (2708, 2710) formed on the first elongate compression shaft and second elongate compression shaft, respectively, may be generally oval in shape, and sized to receive a hook shaped instrument for removal of the shafts from the surgical site. However, it is also contemplated that the apertures may be shaped and sized in alternate configurations so as to receive other types of instruments, and sutures, for the application of pulling forces on the shafts.

Figure 28:
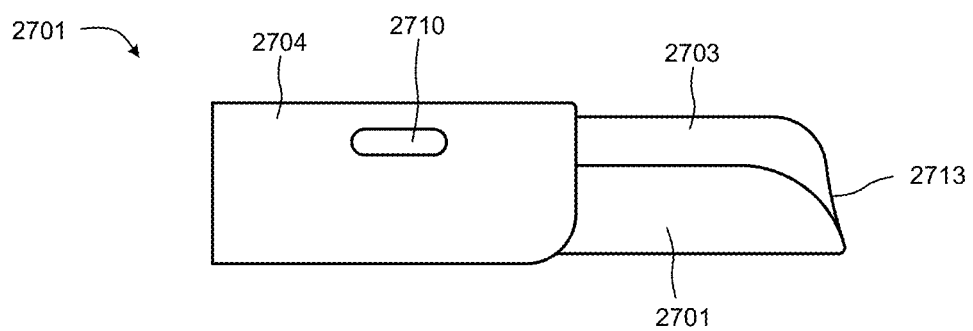
FIG. 28 is a perspective view of an end of the further alternate embodiment of an elongate compression tube depicted in FIG. 27.

Referring now to FIG. 28, shown is a perspective view of an end (2713) of the further alternate embodiment of an elongate compression tube depicted in FIG. 27. In one embodiment, one or both of the respective opposing ends of the compression shafts may be rounded or chamfered to ease the insertion and removal of the shafts from the surgical site, reducing damage to tissue, and decreasing the forces necessary to remove the shafts. In one embodiment, the ends of the compression shafts may also be tapered/flared outwardly such that a mouth (2715) of the respective ends may taper/flare outward to more easily receive a surgical graft being loaded into the elongate compression tube. In one embodiment, the tops of the channel of the first elongate compression channel, at least along inward sections thereof, curls inward towards the middle of the channel.

Figure 29:
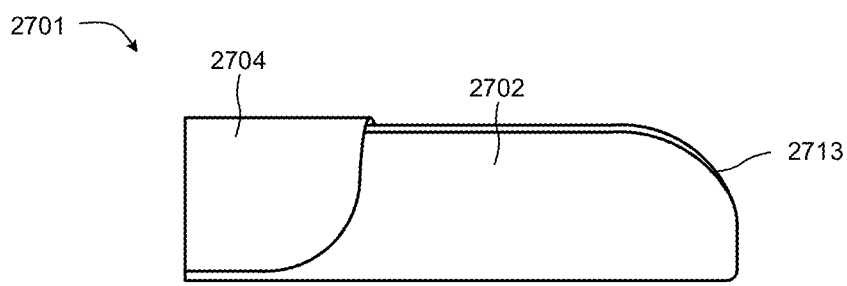
FIG. 29 is a side view of an end of the further alternate embodiment of an elongate compression tube depicted in FIG. 27.

Referring now to FIG. 29, shown is a side view of an end (2713) of the further alternate embodiment of an elongate compression tube depicted in FIG. 27. In one embodiment, one or both of the respective opposing ends of the compression shafts may be rounded or chamfered to ease the insertion and removal of the shafts from the surgical site, reducing damage to tissue, and decreasing the forces necessary to remove the shafts.

Figure 30:
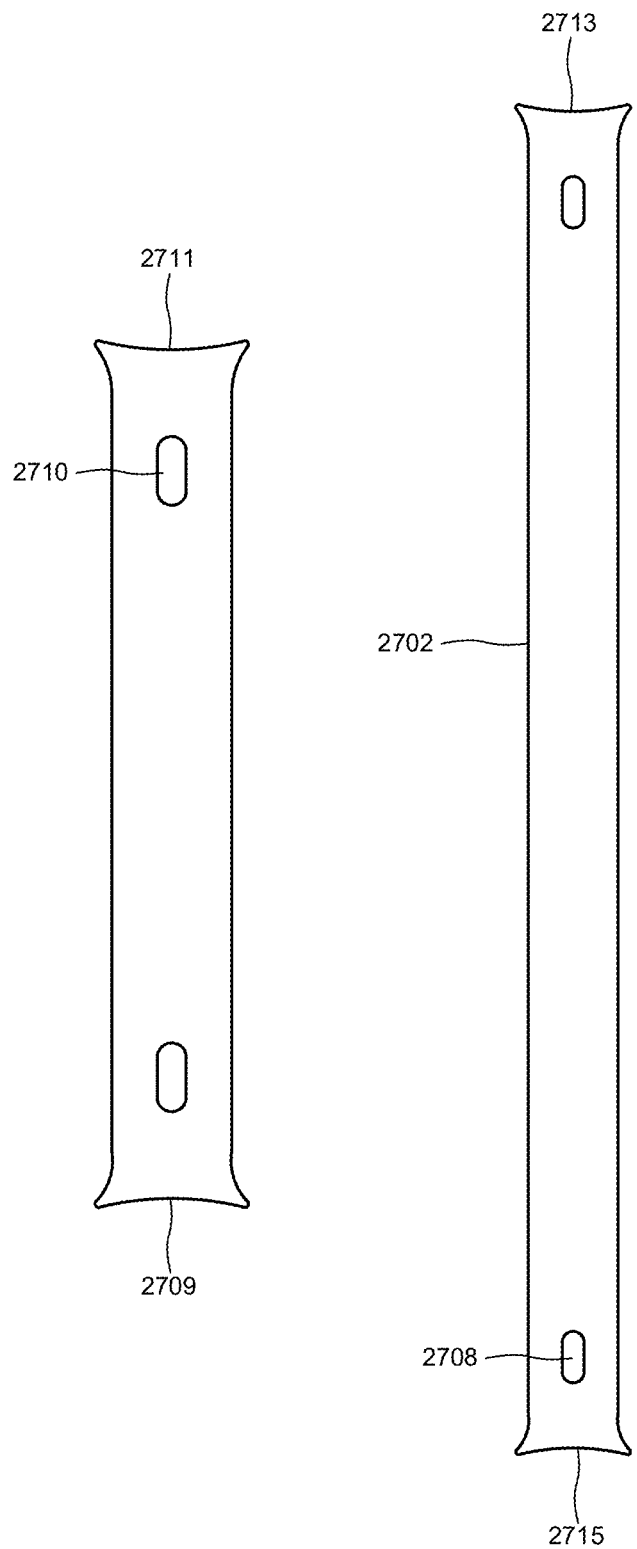
FIG. 30 is a perspective view of the inner sides of the first and second elongate compression shafts of the alternate embodiment of an elongate compression tube depicted in FIG. 27.

Referring now to FIG. 30, a perspective view of the inner sides of the first and second elongate compression shafts of the alternate embodiment of an elongate compression tube (2701) depicted in FIG. 27 is shown. In one embodiment, the one or more apertures (2708, 2710) formed on the first elongate compression shaft and second elongate compression shaft, respectively, may be generally oval in shape, and sized to receive a hook shaped instrument for removal of the shafts from the surgical site. However, it is also contemplated that the apertures may be shaped and sized in alternate configurations so as to receive other types of instruments, and sutures, for the application of pulling forces on the shafts. In one embodiment, one or both of the respective opposing ends of the compression shafts may be rounded or chamfered to ease the insertion and removal of the shafts from the surgical site, reducing damage to tissue, and decreasing the forces necessary to remove the shafts. In one embodiment, the ends of the first and second compression shafts (2713, 2711) may also be tapered/flared outwardly such that a mouths (2709, 2715) of the respective ends may taper/flare outward to more easily receive a surgical graft being loaded into the elongate compression tube.

As previously noted herein, the graft compression system described and depicted herein provides many advantages in the field of ACL reconstruction surgery, and also in connection with other types of surgeries involving the use of grafts. One advantage realized is that the graft compression system is capable of being easily sterilized as it is composed of relatively simple and easily assembled/disassembled components. Another advantage of the graft compression system is that it is capable of being manually operated by surgeons and other operating room personnel, requiring only the use of simply hand tools to actuate the compression system. Another advantage of the graft compression system is that it is capable of effectively reducing the overall volume of a graft, meaning that surgeons will be able to significantly reduce the size/volume of bone tunnels and sockets. Thus, as a result, patients will experience less tissue trauma, swelling, and pain.

Other advantages of the graft compression system and its ability to effectively reduce the diameter of a graft, arise from the relatively "tight" fit of the graft within the bone tunnel or socket into which it may be inserted. Once inserted, the graft will rehydrate and expand, creating a biologic compressive fixation within such bone tunnel or socket. Such a compressive fit will result in a well-fixed graft, making it unnecessary to utilize interference screws and buttons to affix the graft. The nature of the well-fixed graft arising from the use of compressed grafts will also act to minimize micro-motion, thus reducing scarring. Other benefits arising from use of the graft compression device include faster tissue recovery, improved healing environment, creates negative pressure which pulls marrow elements/growth factors into the graft, and results in overall improved outcomes. A graft board is commonly used in graft assembly and preparation. After a graft is prepared, it is place under tension to take all of the creep out of the graft before it is inserted into the patient. One additional advantage arising from the use of the graft compression systems described herein is that compression of the graft results in lengthening of the graft by up to 5 millimeters, which will in some scenarios eliminate the need for graft tensioning.

Figure 31:
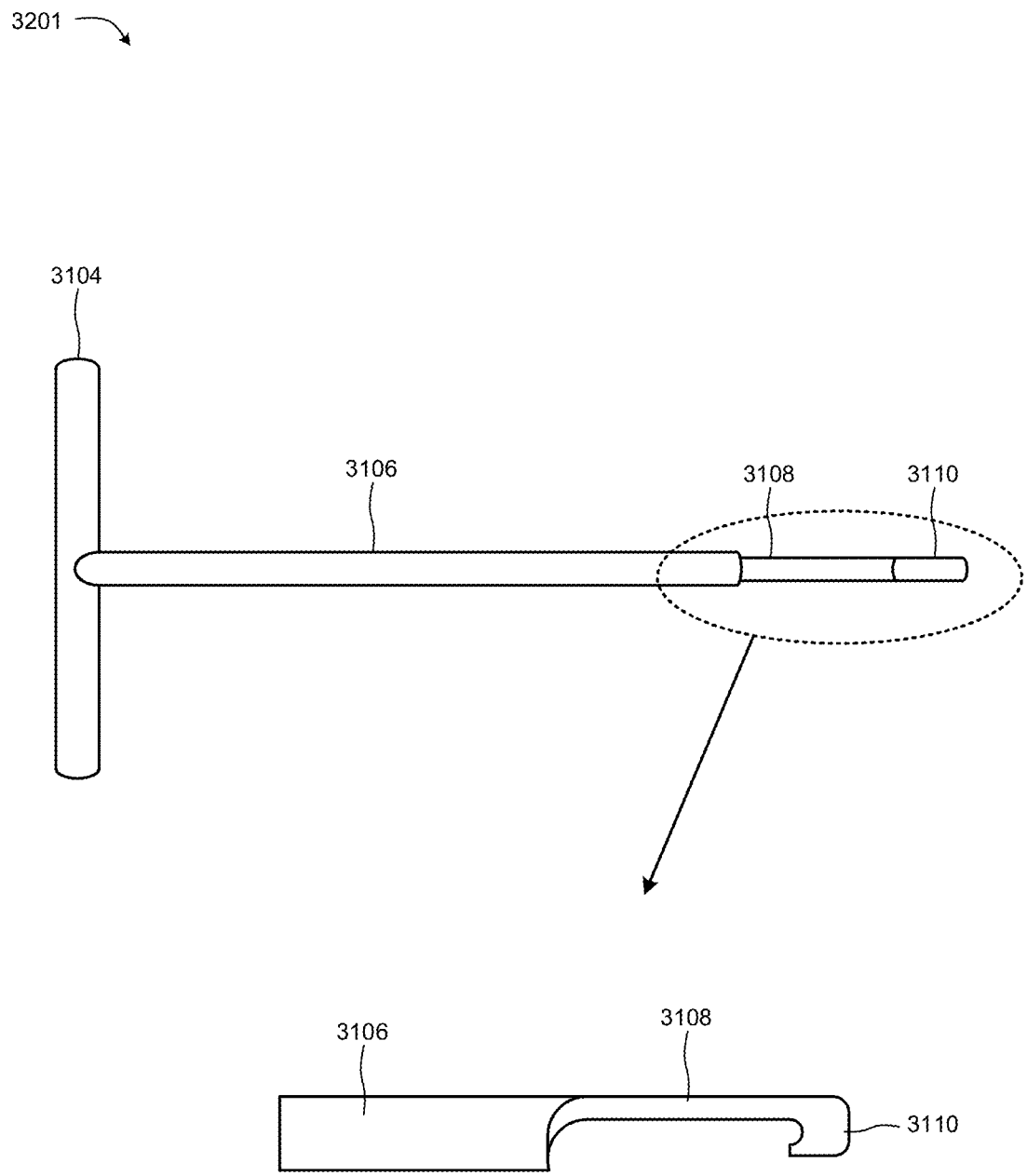
FIG. 31 are perspective views of an alternate embodiment of an elongate hook device configured to remove embodiments of the insertion cap and compression tube following delivery of the graft to the surgical site.

Referring now to FIG. 31, shown are perspective views of an alternate embodiment of an elongate hook device (3102) configured to remove embodiments of the insertion cap (2102) and compression tube following delivery of the graft to the surgical site. In one embodiment, the elongate hook device includes a "T" handle (3104) fastened or affixed onto a proximal end and connected to an elongate shaft (3106) having a length that will permit a distal mounted hook end (3110) to reach a surgical site. In one embodiment, the hook end (3110) comprises a reduced thickness shank (3108) formed on a distal end of the elongate shaft, terminating in a curved hood end (3110) that is shaped and sized to engage a correspondingly shaped and sized slot (see FIG. 21 at 2110) of an insertion cap (see FIG. 21 at 2102). The width of the reduced thickness shank and hood end has a thickness that is small enough for insertion into the slots of the insertion cap and compression shaft apertures. Using the elongate hook device, or another instrument having a hook, a surgeon can insert the device/instrument into the incision and engage the slot (see FIG. 21 at 2110) of the insertion cap (mounted to end of compression tube) at the surgical site to remove the cap from the compression tube and pull it from the patient. Likewise, using the elongate hook device, or another instrument having a hook, a surgeon can insert the device/instrument into the incision and engage the apertures (see FIG. 27 at 2708, 2710) of the compression shafts to remove them from the patient upon successful delivery of the surgical graft.

Figure 32:
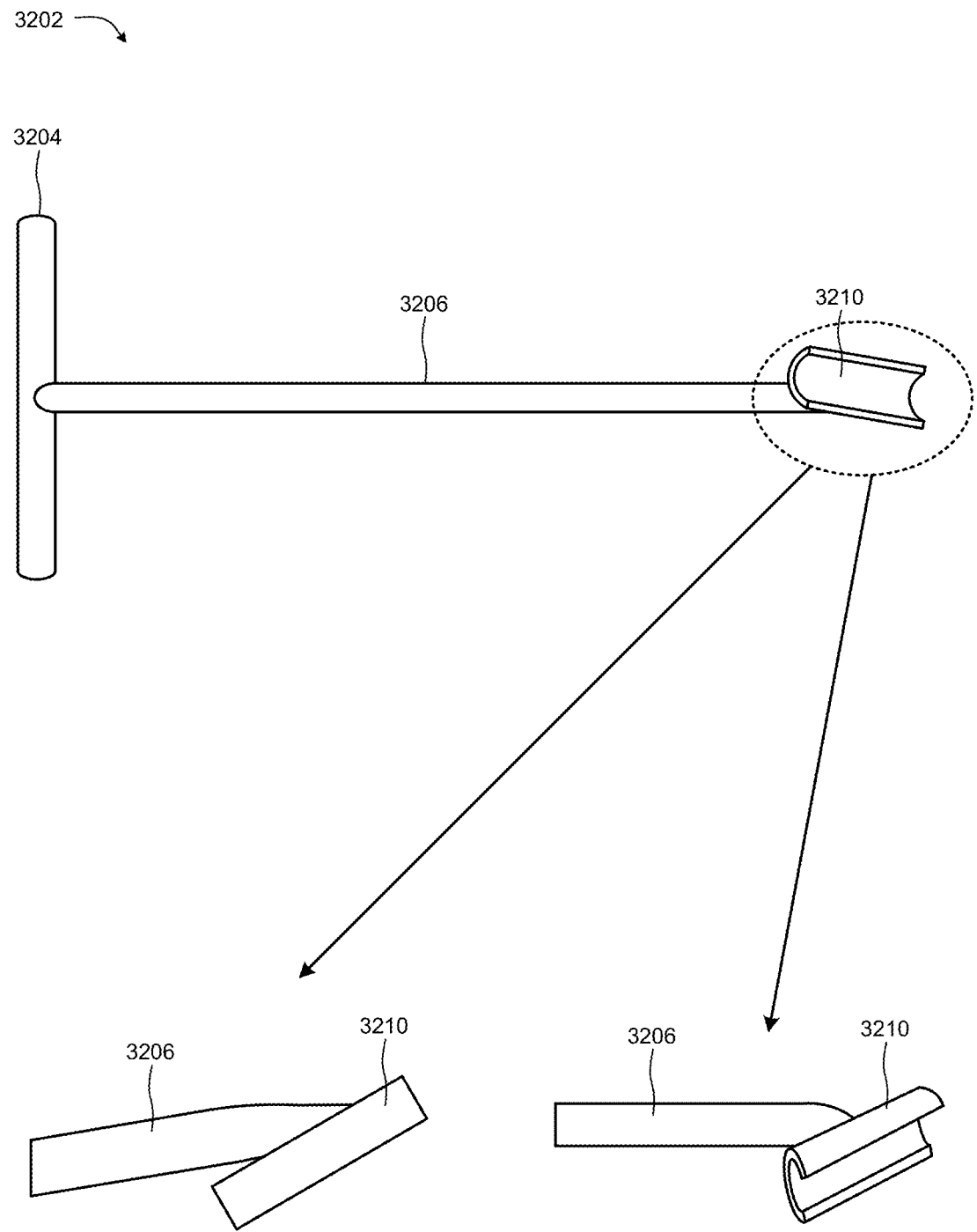
FIG. 32 are perspective views of an alternate embodiment of an elongate push rod.

Referring now to FIG. 32, are perspective views of an alternate embodiment of an elongate push rod (3202) having an elongate rod shaft (3206) positioned intermediate to a proximally positioned flat strike plate (3204), and a distally positioned hollow receptor (3210). In one embodiment, the distally positioned hollow receptor (3210) is semicylindrical (longitudinal half of a cylinder) and has a lumen with opposing open ends, the lumen sized to receive and temporarily mate with an end of a first elongate compression shaft of an elongate compression tube. The hollow receptor (3210), is configured to slide onto the end of the first elongate compression shaft such that a pushing force applied at the strike plate (3204) is transferred through the shaft (3206) and applied at the first elongate compression shaft to assist in pushing the compression tube into embodiments of the graft compression system (for example, see FIG. 18 at 1802). In one embodiment, a mallet may be used to strike the strike plate, thereby pushing the compression tube into the graft compression system. In one embodiment, the connection between the shaft (3206) and receptor (3210) is fixed. In other embodiments, the shaft (3206) and receptor (3210) are pivotally attached (for example, ball and socket joint, hinged joint). An advantage of utilizing the elongate push rod is that a pushing force can be applied to insert the compression tube into the graft compression system without damaging the sutures, the compression tube, or the surgical graft.

Figure 33:
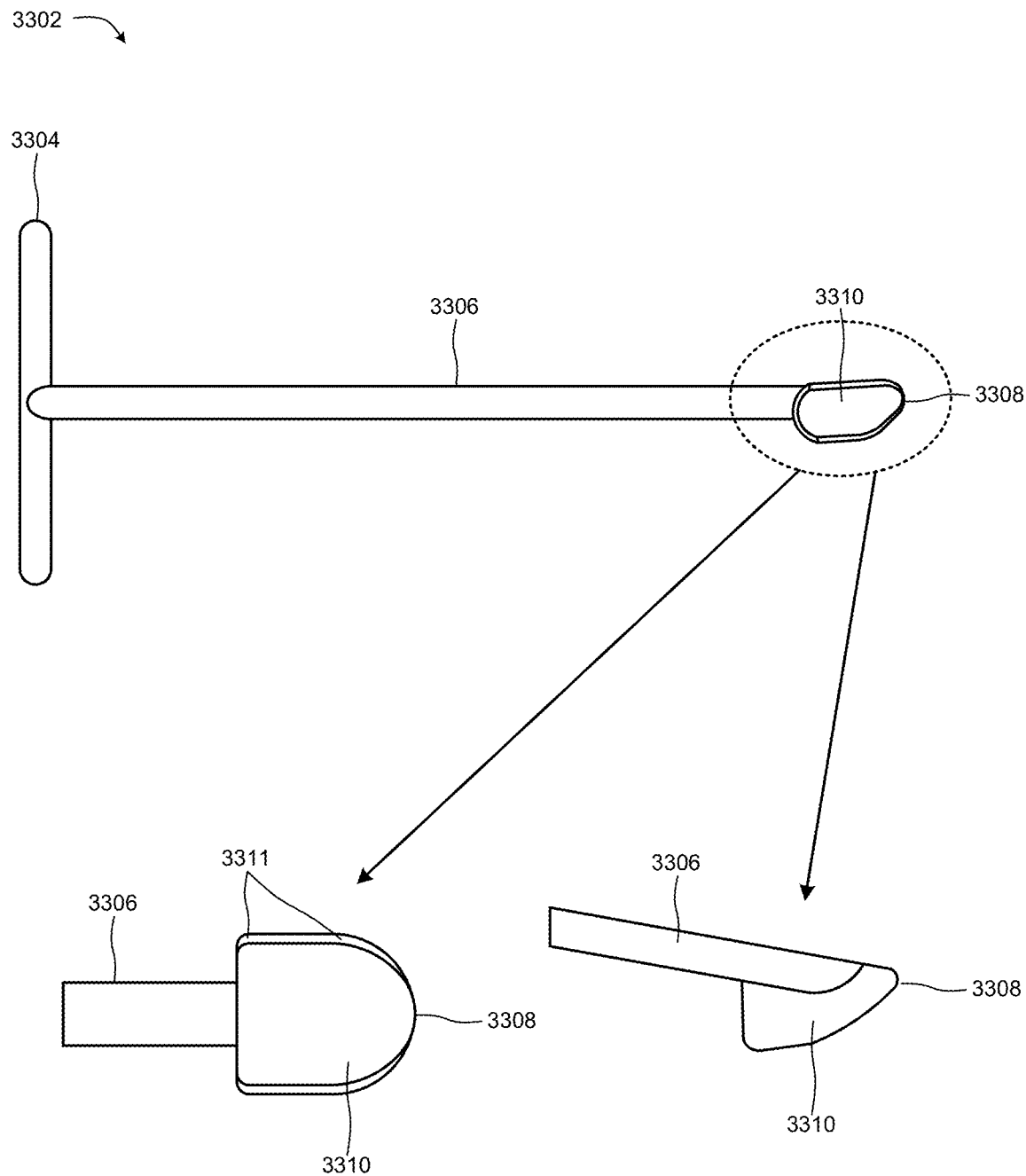
FIG. 33 are perspective views of an embodiment of an elongate guide rod.

Referring now to FIG. 33, are perspective views of an embodiment of an elongate guide rod (3302) having an elongate rod shaft (3306) positioned intermediate to a proximally positioned handle (3304), and a distally positioned guide receptor (3210). In one embodiment, the distally positioned guide receptor (3210) has a proximal portion (3311) that is semicylindrical in shape, and a distal portion that tapers continuously to a blunted point (3308). A channel is formed by the interior surfaces of the proximal portion and distal portion of the distally positioned guide receptor, which is sized and shaped to receive and temporarily mate with a forward end of a first elongate compression shaft, or a forward end of an insertion cap (see FIG. 21 at 2102). In one embodiment, the connection between the shaft (3306) and receptor (3310) is fixed. In other embodiments, the shaft (3306) and receptor (3310) are pivotally attached (for example, ball and socket joint, hinged joint). An advantage of utilizing the elongate guide rod is that due to the tapered distal portion of the guide receptor, having a blunted point, it can be utilized to guide an elongate compression tube into a surgical incision point without causes unnecessary tissue damage.

Figure 34:
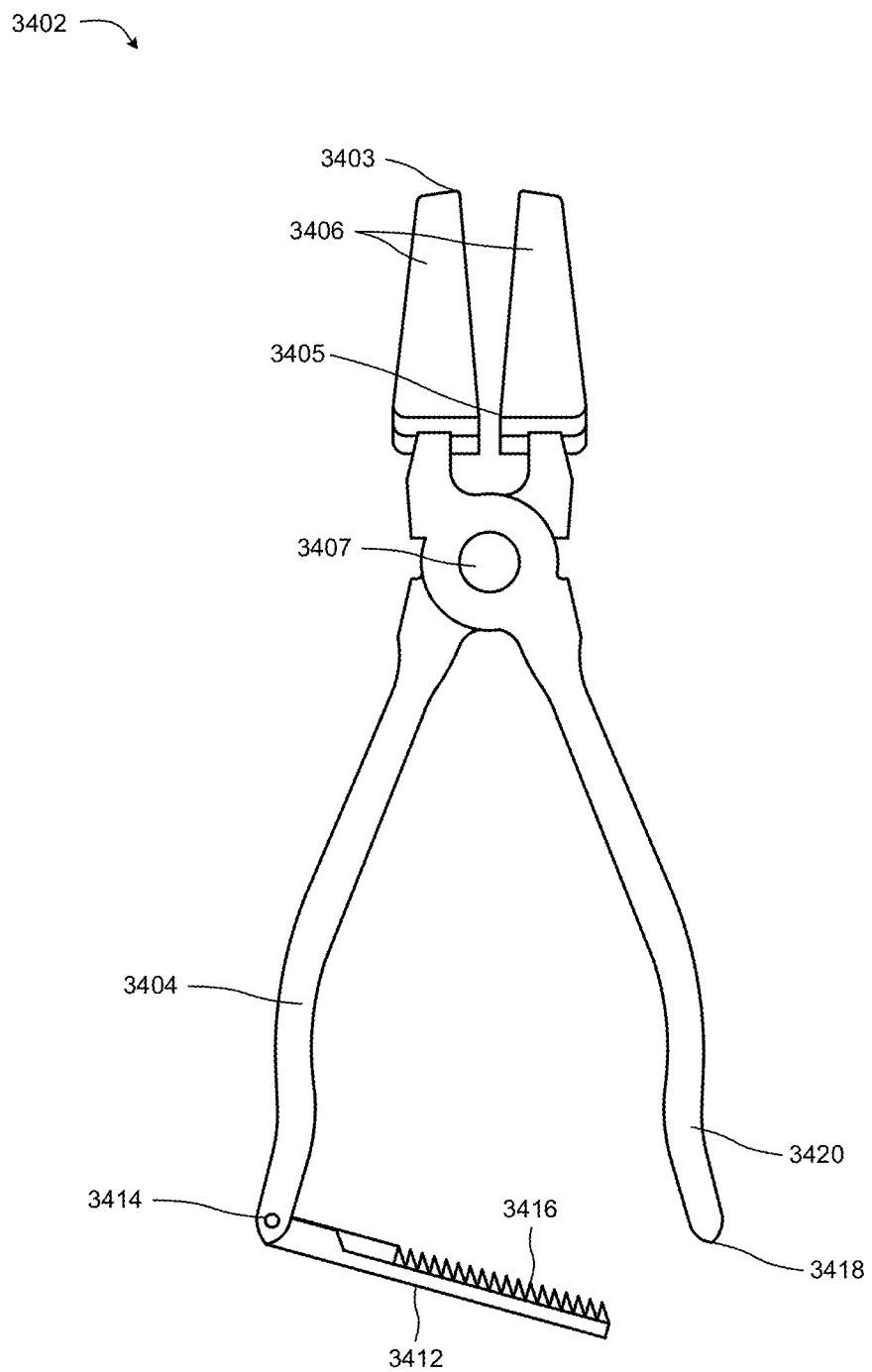
FIG. 34 is a side view of an alternate embodiment of a sequentially compressing pliers.
Figure 35:
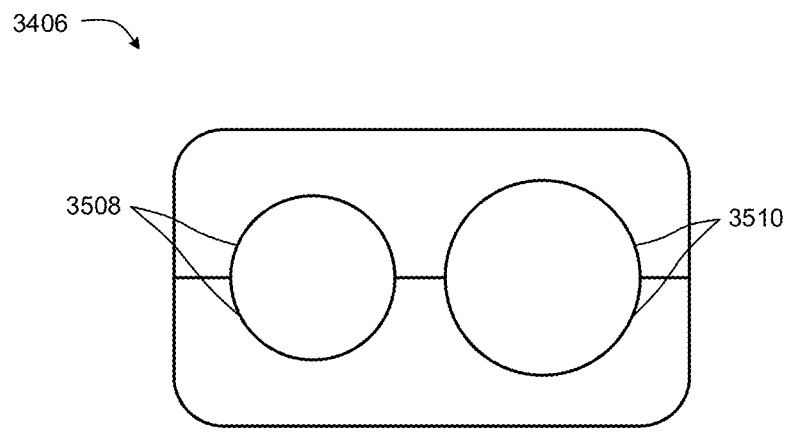
FIG. 35 is a front view of the alternate embodiment of a sequentially compressing pliers depicted in FIG. 34, shown in a closed configuration.
Figure 36:
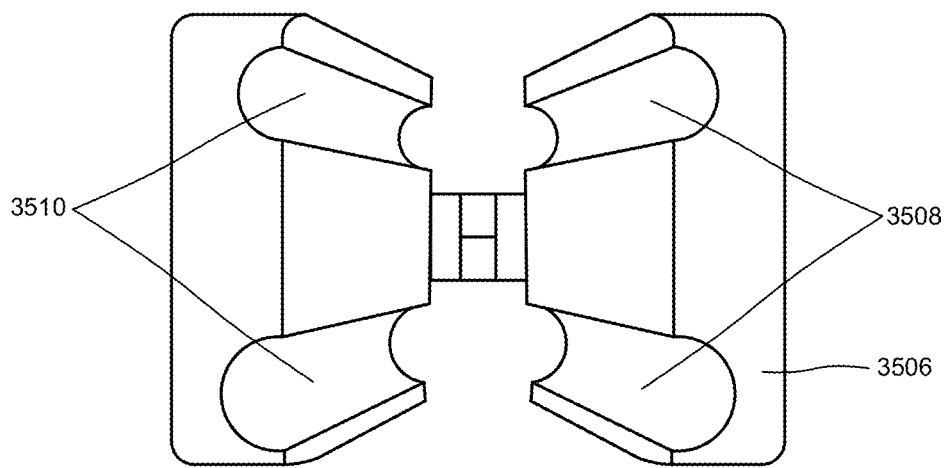
FIG. 36 is a front view of the alternate embodiment of a sequentially compressing pliers depicted in FIG. 34, shown in an open configuration.

Referring now to FIG. 34, a side view of an alternate embodiment of a sequentially compressing pliers (3402) for progressively compressing an elongate compression tube loaded with a surgical graft. In one embodiment, the pliers include handles (3404) for applying a compressive force at the jaws (3406) of the pliers. The plier handles are connected to one another via a first pivot pin (3407). The inside surfaces of the pliers' jaws have semi-circular shaped channels, running longitudinally from the distal end (3403) of the plier jaws, to the proximal end (3405) of the plier jaws. Referring also to FIG. 35, a front view of the alternate embodiment of a sequentially compressing pliers depicted in FIG. 34, shown in a closed configuration, and FIG. 36, a front view of the alternate embodiment of a sequentially compressing pliers depicted in FIG. 34, shown in an open configuration, the semi-circular channels (3508, 3510) are shaped and sized to engage the outer surface of a correspondingly shaped and sized elongate compression tube loaded with a surgical graft. A plurality of semi-circular indentations area formed on the jaws of the pliers, each channel on one jaw having a corresponding semi-circular channel formed on the opposite jaw of the pliers as depicted in FIGS. 35 and 36. In one embodiment, a first set of semi-circular channels (3508) formed on opposing inside surfaces of the jaws have a smaller diameter as compared to an adjacent second set of semi-circular channel (3510) formed on the pliers jaw. The semi-circular indentations are configured to be utilized for compressing and holding an elongate compression tube loaded with a surgical graft. A user may utilize the pliers, applying a compressive force on the handles, to compress a compression tube inserted between a set of semi-circular indentations (3510). Then, in a sequential manner, the compression tube may be engaged by the smaller diameter set of semi-circular indentations (3508) and compressed again. In this manner, the pliers may be utilized to progressively compress the compression tube. In one embodiment, utilization of the pliers may provide a preliminary compression of the compression tube prior to further compression utilizing other compression devices described herein.

Still referring to FIG. 34, in one embodiment, a locking bar (3412) is utilized to maintain a compressive force at the jaws (3406) by maintaining a compressive inward force on the handles of the pliers. The locking bar has in one embodiment two opposing ends. In one embodiment, a first end of the locking bar (3412) is pivotally attached to a proximal end of handle shaft via a second pivot pin (3414). A plurality of grooves (3416) are formed on a distal side of the locking bar, with each groove being capable of engaging a notch (3418) on the proximal end of the other handle shaft (3420). One a groove engages the notch, the groove and notch will remain engaged until a user further compresses the handles to release such engagement. The locking bar is capable of pivoting about the pin (3414) to allow a user to engage the desired groove (3416) on the notch (3418) so as to lock the two handles together according to a desired compressive force. In this manner, the pliers can be locked at a desired compressive force for a duration of time without it being necessary for a user to continue squeezing the handles together. To release the groove/notch engagement, the user must further compress the handles of the pliers, and will allow the locking bar to be pivoted away from the second handle (3420).

Figure 37:
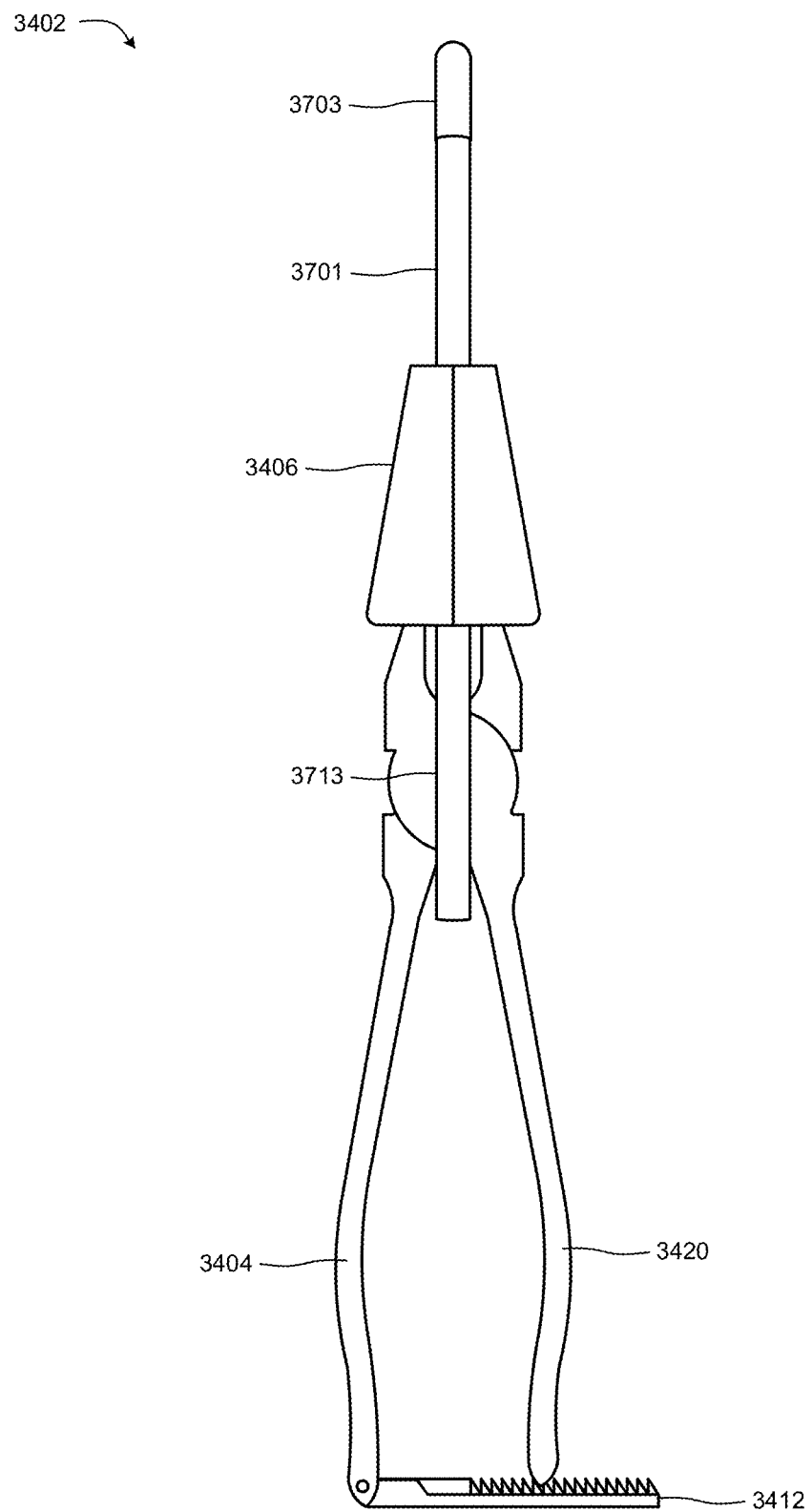
FIG. 37 is a side view of the alternate embodiment of a sequentially compressing pliers depicted in FIG. 34, shown grasping an embodiment of an elongate compression tube.

Referring now to FIG. 37, shown is a side view of the alternate embodiment of a sequentially compressing pliers (3402) depicted in FIG. 34, shown grasping an embodiment of an elongate compression tube (3701). The elongate compression tube (3704), onto which is mounted an insertion cap (3703), has been inserted into one of the compression channels (see FIGS. 35 and 36 at 3508, 3510) formed within the jaws (3406) of the compressing pliers. The elongate compression tube is capable of sliding through compression channels when a user releases pressure of the handles of the pliers such that the entire compression tube can be compressed, segment by segment, within the jaws of the pliers. The compression channels have distal and proximal openings on the distal and proximal ends of the jaws, respectively, which allows for distal and proximal sections of the compression tube to protrude from such openings. As depicted in FIG. 37, a proximal end (3713) of the compression tube (3701) protrudes from the proximal ends of the closed jaws of the pliers. A groove of the locking bar (3412) as described above is depicted in FIG. 37 as having engage the notch on the second handle (3420) to as lock the compressive force of the jaws. To release the groove/notch engagement, the user must further compress the handles of the pliers, and will allow the locking bar to be pivoted away from the second handle (3420).

The inventions described herein may be embodied in other specific forms without departing from the spirit or essential characteristics thereof. The present embodiments are therefore to be considered in all respects as illustrative and not restrictive. Accordingly, the scope of the invention is established by the appended claims rather than by the foregoing description. All changes that come within the meaning and range of equivalency of the claims are embraced therein.

I claim:

1. A surgical graft compression system comprising:
    an upper press body having a first end and opposing second end, said upper press body having a first inner side having a first plurality of parallel semi-circular shaped channels formed thereon; and
    a lower press body having a third end and opposing fourth end, said lower press body having a second inner side having a second plurality of parallel semi-circular shaped channels formed thereon,
    wherein said upper press body is pivotally coupled to said lower press body at said first end and said third end, respectively,
    wherein each of said first plurality of parallel semi-circular shaped channels are formed to have sequentially decreasing channel widths,
    wherein each of said second plurality of parallel semi-circular shaped channels are formed to have sequentially decreasing channel widths,
    wherein said upper press body and said lower press body are configured to pivot about a pivot pin such that said first inner side of said upper press body abuts said second inner side of said lower press body such that said first plurality of parallel semi-circular shaped channels are substantially aligned with said a said plurality of parallel semi-circular shaped channels,
    wherein said pivot pin has opposing ends each having lengths that protrude beyond the respective lateral sides of said upper press body and said lower press body.

2. The surgical graft compression system of claim 1, further comprising a screw press barrel that is attached to an upper portion of a threaded eye bolt shaft, a lower portion of said eye bolt shaft having an eyelet formed thereon and is pivotally coupled to said fourth end of said lower press body via a pin.

3. The surgical graft compression system of claim 2, wherein one or more outwardly projecting handles are attached to said screw press barrel.

4. The surgical graft compression system of claim 3, wherein a bottom end of said screw press barrel is configured to abut an outer side of said upper press body to compress said upper press body with said lower press body.

* * * * *